US008518968B2

(12) United States Patent
Wiestner et al.

(10) Patent No.: US 8,518,968 B2
(45) Date of Patent: Aug. 27, 2013

(54) HYDRAZONE AND DIACYL HYDRAZINE COMPOUNDS AND METHODS OF USE

(75) Inventors: Adrian Wiestner, Bethesda, MD (US); Yihong Ye, Potomac, MD (US); Qiuyan Wang, Rockville, MD (US); William C. Trenkle, Bethesda, MD (US); Bidhan A. Shinkre, Ponda (IN)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 0 days.

(21) Appl. No.: 13/513,819

(22) PCT Filed: Dec. 3, 2010

(86) PCT No.: PCT/US2010/058849
§ 371 (c)(1),
(2), (4) Date: Aug. 10, 2012

(87) PCT Pub. No.: WO2011/069039
PCT Pub. Date: Jun. 9, 2011

(65) Prior Publication Data
US 2012/0316198 A1 Dec. 13, 2012

Related U.S. Application Data

(60) Provisional application No. 61/266,760, filed on Dec. 4, 2009.

(51) Int. Cl.
| | | |
|---|---|---|
| *A61K 31/341* | (2006.01) | |
| *A61K 31/4178* | (2006.01) | |
| *A61K 31/443* | (2006.01) | |
| *A61K 31/4725* | (2006.01) | |
| *C07D 405/12* | (2006.01) | |
| *C07D 233/36* | (2006.01) | |
| *C07D 217/26* | (2006.01) | |
| *C07D 307/75* | (2006.01) | |

(52) U.S. Cl.
USPC ........... 514/309; 514/472; 514/392; 514/336; 549/481; 548/315.7; 548/321.5; 546/284.7; 546/142

(58) Field of Classification Search
USPC ................ 514/309, 472, 392, 336; 549/481; 548/315.7, 321.5; 546/284.7, 142
See application file for complete search history.

(56) References Cited

U.S. PATENT DOCUMENTS

| | | | |
|---|---|---|---|
| 4,794,120 | A | 12/1988 | Manoury et al. |
| 2002/0019539 | A1 | 2/2002 | Bailey et al. |
| 2002/0091148 | A1 | 7/2002 | BaMaung et al. |

FOREIGN PATENT DOCUMENTS

| | | |
|---|---|---|
| EP | 1279729 A1 | 1/2003 |
| GB | 2325932 A | 12/1998 |
| WO | 9708150 | 3/1997 |
| WO | 9736892 A1 | 10/1997 |
| WO | 0153297 A1 | 7/2001 |
| WO | 02089745 A2 | 11/2002 |
| WO | 2005037257 A2 | 4/2005 |
| WO | 2009011910 A2 | 1/2009 |

OTHER PUBLICATIONS

Cancer [online], [retrieved on Jul. 6, 2007] Retrieved from the Internet, URL: http://www.nlm.nih.gov/medlineplus/cancer.html.*
Lala et al., Role of nitric oxide in tumor progression: Lessons from experimental tumors, Cancer and Metastasis Reviews (1998), 17, 91-106.*
Golub et al., Molecular Classification of Cancer: Class Discovery and Class Prediction by Gene Expression Monitoring, Science (1999), vol. 286, 531-537.*
Fiebiger et al., "Dissection of the Dislocation Pathway for Type I Membrane Proteins with a New Small Molecule Inhibitor, Eeyarestatin" Molecular Biology of the Cell, vol. 15, Apr. 2004, pp. 1635-1646.
Hein et al., "Effects of Nitrofurylpropenylidene Benzhydrazides Against Trichomonads, Bacterial, Yeasts and Fungi with Particular Consideration of the Results in the Ames Test and Host-Mediated Assay" Arzneimittel-Forschung, vol. 33, Issue 3, 1983, Abstract Only.
Lin et al., "Endoplasmic Reticulum Stress in Disease Pathogenesis" Annual Review of Pathology: Mechanisms of Disease, vol. 3, 2008, pp. 399-425.
International Search Report; International Application No. PCT/2008/008797, International Filing Date; Jan. 22, 2009; Date of Mailing: Mar. 9, 2009.
International Preliminary Report on Patentability; International Application No. PCT/US/2010/058849, International Filing Date; Dec. 3, 2010; Date of Mailing; Jun. 5, 2012; 8 Pages.
International Search Report; International Application No. PCT/US/2010/058849, International Filing Date; Dec. 3, 2010; Date of Mailing; Apr. 29, 2011, 6 Pages.
Written Opinion; International Application No; International Application No. PCT/US/2010/058849, International Filing Date; Dec. 3, 2010; Date of Mailing; Apr. 29, 2011, 9 Pages.

(Continued)

*Primary Examiner* — Kristin Vajda
(74) *Attorney, Agent, or Firm* — Cantor Colburn LLP

(57) ABSTRACT

Disclosed herein are novel hydrazone and diacyl hydrazine derivatives that are inhibitors of the endoplasmic reticulum-associated protein degradation (ERAD) pathway. Also disclosed are hydrazone and diacyl hydrazine derivatives as potent and selective inhibitors of the p97 ATPase. These agents provide useful tools for the study of protein degradation and other processes involving p97. Methods of treating diseases or disorders for which p97 inhibition and/or ER stress induction is an effective treatment with certain hydrazone and diacyl hydrazine derivatives are also disclosed.

20 Claims, 9 Drawing Sheets

(56) References Cited

OTHER PUBLICATIONS

Saikachi et al., "Synthesis of Furan Derivatives. XIV Condensation of 2-(5-Nitro)furylacrolein and 2-(5-Nitro) furaldehyde with Hydrazides" Pharm Bull. vol. 3, 1955, pp. 194-199.

Wang et al., "Inhibition of p97-dependent Protein Degradation by Eeyarestatin I", The Journal of Biological chemistry, vol. 283, No. 12, 2008, pp. 7445-7454.

Woodman, "P97, A Protein Coping with Multiple Identities" Journal of Cell Science, 116, 2003, pp. 4283-4290.

* cited by examiner a b c

HYDRAZONE AND DIACYL HYDRAZINE COMPOUNDS AND METHODS OF USE

CROSS REFERENCE TO RELATED APPLICATIONS

This application is a national stage application filed 35 USC §371 of PCT/US2010/058849 which was filed Dec. 3, 2010 and claims priority from U.S. provisional application No. 61/266,760 filed Dec. 4, 2009, both of which is hereby incorporated by reference in its entirety.

STATEMENT OF GOVERNMENT SUPPORT

This invention was made in part with government support from the National Institute of Health. The government has certain rights in this invention.

BACKGROUND

Ubiquitin-mediated proteolysis is an important pathway of non-lysosomal protein degradation that controls the timed destruction of many cellular regulatory proteins. Ubiquitin is an evolutionarily highly conserved 76-amino acid polypeptide, which is abundantly present in eukaryotic cells. The ubiquitin pathway leads to the covalent attachment of polyubiquitin chains to target substrates, which are then degraded by a multi-catalytic proteasome complex. In addition to its role in proteasomal degradation of target proteins, the ubiquitin system is also involved in a number of cellular processes unrelated to proteasomal degradation including endocytosis, trafficking in the endosomal system, viral budding, DNA repair, nucleocytoplasmic trafficking, and kinase activation.

In eukaryotic cells the ubiquitin proteasome system (UPS) plays an important role in many protein quality control pathways, including the elimination of misfolded proteins from the endoplasmic reticulum (ER). The UPS dependent degradation of misfolded ER proteins by the so called ERAD pathway (ER-associated protein degradation) adapts cells to stress conditions that would other wise disturb ER homeostasis and cause programmed cell death.

To degrade misfolded ER proteins, terminally misfolded polypeptides (both membrane and soluble substrates) are recognized by chaperones, and targeted to the export sites at the ER membrane. Polypeptides are subsequently transferred across the membrane via an unknown conduit to enter the cytosol where they become substrates of the UPS. A cytosolic ATPase named p97 and a dimeric cofactor Ufd1-Np14 act together to extract misfolded proteins from the ER membranes once these substrates have undergone polyubiquitination. p97 also interacts with several deubiquitinases, which remodulate polyubiquitin chains on p97 substrates while these substrates are being transferred to the proteasome. Once the polyubiquitinated substrates are delivered to the proteasome, they are rapidly degraded.

In addition to its role in the ERAD pathway, p97 ATPase is also involved in many other ubiquitin-dependent biological processes critical for cell viability, including cell cycle regulation, transcription control, membrane fusion, and protein trafficking.

The retrotranslocation pathway can be hijacked by certain viruses to downregulate the expression of correctly folded cellular proteins involved in the immune defense of cells, allowing these viruses to propagate without being detected by the cytotoxic T cells. For example, either of the two proteins US11 and US2 encoded by human cytomegalovirus (HCMV) is able to induce rapid dislocation and degradation of newly synthesized MHC class I heavy chains.

Cancer is a class of diseases in which a group of cells display uncontrolled growth, intrusion on and destruction of adjacent tissue), and sometimes metastasis (spreading to other locations in the body via lymph or blood). The development of cancer can depend on the accumulation of specific genetic alterations that allow aberrant cell proliferation. The ubiquitin-proteasome system plays a significant role in cell cycle progression, which is essential for the survival of cancer cells. Compounds that disturb the ubiquitin pathways affect cell growth and other cellular functions and may therefore offer therapeutic possibilities against cancer.

Eeyarestatins are promising anti-cancer and antiviral agents with a novel mechanism of action. The two structurally related chemicals termed Eeyarestatin I and II were originally identified by screening a chemical library containing 16,320 compounds for inhibitors of endoplasmic reticulum (ER) associated protein degradation (ERAD or retrotranslocation). Eeyarestatins can induce cancer cell death either as a single agent or synergize with bortezomib, a proteasome inhibitor, for increased cytotoxic activity. Bortezomib is approved in the United States for treatment of multiple myeloma and mantle cell lymphoma and marketed under the name VEL-CADE® (Millenium Pharmaceuticals, Inc.).

The anti-cancer and antiviral activities of Eeyarestatin I (EERI) can be attributed at least in part to its ability to disturb ubiquitin homeostasis and block ERAD. ER stress elicited in EERI-treated cells, together with ubiquitin stress, causes cells to undergo apoptosis. Eeyarestatins interact with a p97 ATPase complex to inhibit ERAD by blocking the retrotranslocation of misfolded ER substances and the disassembly of ubiquitin chains attached to these substrates. (WO 2009/011910) The use of EERI in cancer therapy has been described and the antiviral activity of EERI, including the antiretroviral activity, has been demonstrated. The interaction of EERI with the p97 complex appears to negatively influence a deubiquitinating process that is mediated by p97-associated deubiquitinating enzymes. In particular, the p97-associated deubiquitinating enzyme ataxin-3 is among those affected by EERI. As a result, polyubiquitin conjugated proteins are accumulating in cells treated with EERI, an indication of disruption of ubiquitin homeostasis.

While EERI and II have important biological and therapeutic activities, synthesis of these compounds is difficult and labor-intensive. There remains a need in the art for compounds with biological and therapeutic activities similar to EERI, but for which the synthesis is easier and more cost-effective.

SUMMARY

Described herein are hydrazone and diacyl hydrazine compounds (diamides), their methods of manufacture, compositions containing the hydrazone and diacyl hydrazine compounds, and methods of use of both the hydrazone and diacyl hydrazine compounds and compositions thereof. Included herein, is a method of treating a disease or disorder responsive to p97 inhibition and/or ER stress induction or a viral infection in a patient, comprising providing a therapeutically effective amount of a hydrazone or diacylhydrazone ERAD inhibitor to the patient.

Further included herein is a method of treating a disease or disorder responsive to p97 inhibition and/or ER stress induction or viral infection in a patient comprising providing a therapeutically effective amount of a compound or pharmaceutically acceptable salt thereof of Formula I or Formula II

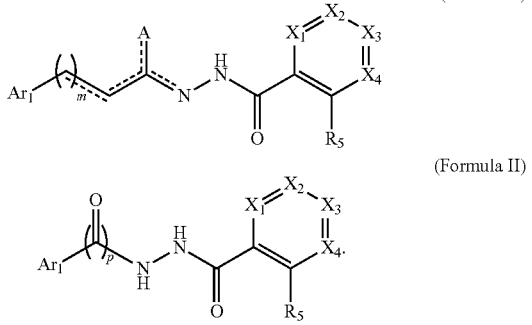

(Formula I)

(Formula II)

Within Formula I dashed lines indicate a single or double covalent bond.

A is hydrogen or oxo (=O).

$Ar_1$ is furanyl, thienyl, pyridyl, or phenyl, each of which is optionally substituted with one or more substituents independently chosen from halogen, hydroxyl, amino, cyano, nitro, —CHO, —COOH, —PO$_4$, $C_1$-$C_4$alkyl, $C_1$-$C_4$alkoxy, $C_2$-$C_4$alkanoyl, $C_1$-$C_4$alkylester, mono- and di-($C_1$-$C_4$)alkylamino, $C_1$-$C_2$haloalkyl, and $C_1$-$C_2$haloalkoxy.

The variable m is 1, 2, 3, 4, or 5.

The variable p is 0 or 1.

$X_1$ is $CR_1$ or N; $X_2$ is $CR_2$ or N; $X_3$ is $CR_3$ or N; and $X_4$ is $CR_4$ or N; wherein no more than 2 of $X_1$-$X_4$ are N.

$R_1$ to $R_4$ are independently chosen from hydrogen, halogen, hydroxyl, amino, cyano, nitro, $C_1$-$C_4$alkyl, $C_1$-$C_4$alkoxy, mono- and di-($C_1$-$C_4$)alkylamino, $C_1$-$C_2$haloalkyl, and $C_1$-$C_2$haloalkoxy.

$R_5$ is hydrogen, halogen, hydroxyl, amino, cyano, nitro, $C_1$-$C_4$alkyl, $C_1$-$C_4$alkoxy, mono- or di-($C_1$-$C_4$)alkylamino, $C_1$-$C_2$haloalkyl, or $C_1$-$C_2$haloalkoxy.

One of the following conditions may be present:

$R_1$ and $R_2$ are taken together to form a 6-membered carbocyclic ring, or a 5- or 6-membered heterocyclic ring containing 1 or 2 heteroatoms independently chosen from N, O, and S, which carbocyclic or heterocyclic $R_1$/$R_2$ ring is substituted with 0 or 1 or more substituents independently chosen from halogen, hydroxyl, amino, cyano, nitro, $C_1$-$C_4$alkyl; or $R_2$ and $R_3$ are taken together to form a 6-membered carbocyclic ring, or a 5- or 6-membered heterocyclic ring containing 1 or 2 heteroatoms independently chosen from N, O, and S, which carbocyclic or heterocyclic $R_2$/$R_3$ ring is substituted with 0 or 1 or more substituents independently chosen from halogen, hydroxyl, amino, cyano, nitro, $C_1$-$C_4$alkyl, $C_1$-$C_4$alkoxy, mono- and di-($C_1$-$C_4$)alkylamino, $C_1$-$C_2$haloalkyl, and $C_1$-$C_2$haloalkoxy; or $R_3$ and $R_4$ are taken together to form a 6-membered carbocyclic ring, or a 5- or 6-membered heterocyclic ring containing 1 or 2 heteroatoms independently chosen from N, O, and S, which carbocyclic or heterocyclic $R_3$/$R_4$ ring is substituted with 0 or 1 or more substituents independently chosen from halogen, hydroxyl, amino, cyano, nitro, $C_1$-$C_4$alkyl, $C_1$-$C_4$alkoxy, mono- and di-($C_1$-$C_4$)alkylamino, $C_1$-$C_2$haloalkyl, and $C_1$-$C_2$haloalkoxy; or $R_1$ and $R_2$ are taken together to form a 6-membered carbocyclic ring, or a 5- or 6-membered heterocyclic ring containing 1 or 2 heteroatoms independently chosen from N, O, and S, and $R_4$ and $R_5$ are taken together to form a 6-membered carbocyclic ring, or a 5- or 6-membered heterocyclic ring containing 1 or 2 heteroatoms independently chosen from N, O, and S, thereby forming a three ring system; which three ring system is substituted with 0 or 1 or more substituents independently chosen from halogen, hydroxyl, amino, cyano, nitro, $C_1$-$C_4$alkyl.

Further provided herein are compounds of Formula I and II, and pharmaceutical formulations comprising a compound or pharmaceutically acceptable salt of Formula I or II together with a carrier.

Also described herein is a method of inhibiting p97 and/or inducing ER stress in a cell, comprising contacting the cell with a concentration of a compound or salt sufficient to significantly modulate p97 activity at the ER membrane, wherein the compound is a compound Formula I. In certain embodiments the cell is present in a human subject and the modulation is a significant block of p97 function, resulting in disruption of deubiquitination associated with the p97 complex.

Also described herein is the discovery of a molecular module that is capable of targeting a compound to the membrane of the endoplasmic reticulum to implement a specific cellular effect.

BRIEF DESCRIPTION OF THE DRAWINGS

FIG. 4 presents graphs comparing CBU-028, EERI, and bortezomib with respect to percent cell viability as a function of concentration, measured using JEKO-1 cells stably transfected with shRNAs to luciferase (shLuc, control ■) or Noxa (shNoxa ○). Cells were treated for 24 hours with the indicated drugs. Viability was determined with MTT and normalized to untreated control.

DETAILED DESCRIPTION

Figure 1:
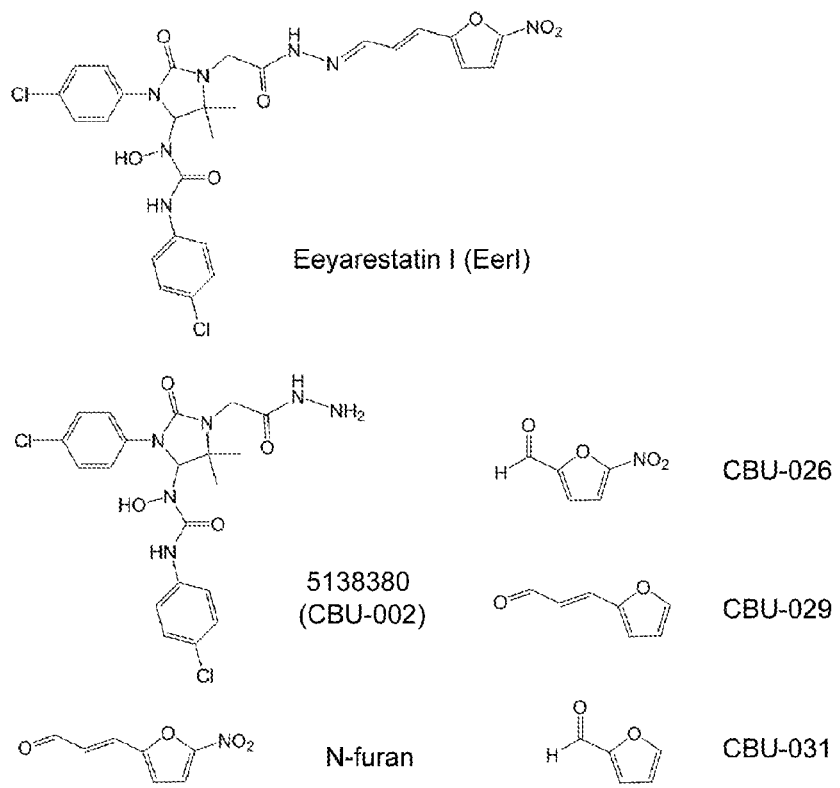
FIG. 1 shows structures of EERI and structurally related compounds (panel a), a graph of the dose-percent viability of JEKO-1 cells treated with EERI or one of the structurally related compounds (panel b), and an image of immunoblot analysis of expression of ATF3, ATF4, NOXA, and p97 in JEKO-1 cells after treatment with EERI or one of the structurally related compounds (panel c)
Figure 1:
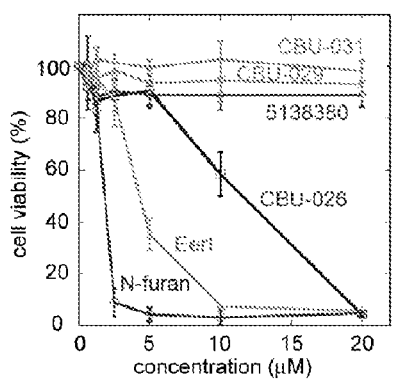
Figure 1:
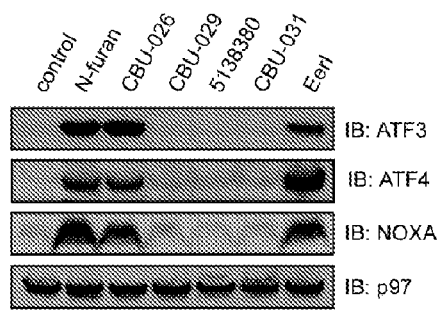

Disclosed herein are novel hydrazone and diacyl hydrazine compounds that are inhibitors of ERAD and can disrupt ubiquitin homeostasis. These compounds are highly active against hematologic tumor cells including cells resistant to the proteasome inhibitor bortezomib. In contrast to EERI, these novel compounds can be synthesized more easily and cost-effectively in large quantities. The compounds disclosed herein can also be used as probes to study the mechanism of protein degradation and other biological processes involving the p97 ATPase. Furthermore, since certain of these compounds are fluorescent and have a high affinity for the ER, they can serve as probes to detect ER structures in live cells and target other molecules to the ER membrane.

Structure activity analysis of EERI was performed. Molecular fragment screening of the nitro-furan and the aromatic domains (FIG. 1, panel a) of EERI showed that the 5-nitrofuryl-acrolein fragment was cytotoxic while the acyl-hydrazine fragment was relatively inert. New compounds varying each of the domains of EERI were then designed, resulting in the novel hydrazone and diacyl hydrazine compounds disclosed herein with EERI-like activities that can be obtained by a single synthetic transformation.

Terminology

Compounds are described using standard nomenclature. Unless defined otherwise, all technical and scientific terms used herein have the same meaning as is commonly understood by one of skill in the art to which this invention belongs.

Formula I includes all substructures of Formula I described herein, for example compounds of Formula III to XI.

The terms "a" and "an" do not denote a limitation of quantity, but rather denote the presence of at least one of the referenced items. The term "or" means "and/or". The terms "comprising", "having", "including", and "containing" are to be construed as open-ended terms (i.e., meaning "including, but not limited to"). Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of any and all examples, or exemplary language (e.g., "such as"), is intended merely provided as illustrative and do not limit the scope in any way unless otherwise claimed. No language in the specification should be construed as indicating any non-claimed element as essential. Unless defined otherwise, technical and scientific terms used herein have the same meaning as is commonly understood by one of skill in the art to which this invention belongs.

All compounds are understood to include all possible isotopes of atoms occurring in the compounds. Isotopes include those atoms having the same atomic number but different mass numbers. By way of general example, and without limitation, isotopes of hydrogen include tritium and deuterium and isotopes of carbon include $^{11}C$, $^{13}C$, and $^{14}C$.

The term "substituted" means any one or more hydrogens on the designated atom or group is replaced with a selection from the indicated group, provided that the designated atom's normal valence is not exceeded. When the substituent is oxo (i.e., =O), then 2 hydrogens on the atom are replaced. When aromatic moieties are substituted by an oxo group, the aromatic ring is replaced by the corresponding partially unsaturated ring. For example a pyridyl group substituted by oxo is a pyridone. Combinations of substituents and/or variables are permissible only if such combinations result in stable compounds or useful synthetic intermediates. A stable compound or stable structure is meant to imply a compound that is sufficiently robust to survive isolation from a reaction mixture, and subsequent formulation into an effective therapeutic agent.

A dash ("-") that is not between two letters or symbols is used to indicate a point of attachment for a substituent.

"Alkyl" includes both branched and straight chain saturated aliphatic hydrocarbon groups, having the specified number of carbon atoms. The term $C_1$-$C_2$alkyl means an alkyl group having from 1 to about 2 carbon atoms, e.g., methyl and ethyl, respectively.

"Alkoxy" means an alkyl group, as defined above, with the indicated number of carbon atoms attached via an oxygen bridge.

"Alkanoyl" is an alkyl group as defined above, attached through a keto (—(C═O)—) bridge. Alkanoyl groups have the indicated number of carbon atoms, with the carbon of the keto group being included in the numbered carbon atoms. For example a $C_2$alkanoyl group is an acetyl group having the formula $CH_3(C═O)$—.

A "6-membered carbocyclic group" is a saturated, partially unsaturated, or aromatic ring containing only carbon ring atoms. Unless otherwise indicated, the carbocyclic group may be attached to its pendant group at any carbon atom that results in a stable structure. When indicated the carbocyclic rings described herein may be substituted on any available ring carbon if the resulting compound is stable. Carbocyclic groups include cycloalkyl groups, such as cyclohexyl; cycloalkenyl groups, such as cyclohexenyl; and aryl groups, such as phenyl.

"Halo" or "halogen" means fluoro, chloro, bromo, or iodo.

"Mono- and/or di-alkylamino" means secondary or tertiary alkyl amino groups, wherein the alkyl groups are as defined above and have the indicated number of carbon atoms. The point of attachment of the alkylamino group is on the nitrogen. The alkyl groups are independently chosen. Examples of mono- and di-alkylamino groups include ethylamino, dimethylamino, and methyl-propyl-amino.

"Haloalkyl" means both branched and straight-chain alkyl groups having the specified number of carbon atoms, substituted with 1 or more halogen atoms, generally up to the maximum allowable number of halogen atoms. Examples of haloalkyl include, but are not limited to, trifluoromethyl, difluoromethyl, 2-fluoroethyl, and penta-fluoroethyl.

"Haloalkoxy" indicates a haloalkyl group as defined above attached through an oxygen bridge (oxygen of an alcohol radical).

A "5- or 6-membered heterocyclic group" is a saturated, partially unsaturated, or aromatic ring containing from 1 or 2 heteroatoms chosen from N, O, and S, with remaining ring atoms being carbon. Unless otherwise indicated, the heterocyclic ring may be attached to the group it substitutes at any heteroatom or carbon atom that results in a stable structure. When indicated the heterocyclic rings described herein may be substituted on carbon or on a nitrogen atom if the resulting compound is stable. It is preferred that the total number of S and O atoms in a heterocyclic group is not more than 2. Examples of 5- and 6-membered heterocyclic groups include pyridyl, pyrimidinyl, pyridizinyl, pyrazinyl, imidazolyl, oxazolyl, furanyl, thiophenyl, thiazolyl, triazolyl, tetrazolyl, isoxazolyl, pyrrolyl, pyrazolyl, furanyl, thienyl, pyrrolyl, pyrazolyl, pyrrolidinyl, morpholinyl, piperazinyl, piperidinyl, and pyrrolidinyl.

Compounds described herein may contain one or more asymmetric elements such as stereogenic centers, stereogenic axes and the like, e.g., asymmetric carbon atoms, so that the compounds can exist in different stereoisomeric forms. These compounds can be, for example, racemates or optically active forms. For compounds with two or more asymmetric elements, these compounds can additionally be mixtures of diastereomers or a single diastereomer of a racemic mixture. For compounds having asymmetric centers, all optical isomers in pure form and mixtures thereof are encompassed. In these situations, the single enantiomers, i.e., optically active forms can be obtained by asymmetric synthesis, synthesis from optically pure precursors, or by resolution of the racemates. Resolution of the racemates can also be accomplished, for example, by conventional methods such as crystallization in the presence of a resolving agent, or chromatography, using, for example a chiral HPLC column. All forms are contemplated herein regardless of the methods used to obtain them.

All forms (for example solvates, optical isomers, enantiomeric forms, polymorphs, co-crystals, free compound and salts) of an active agent may be employed either alone or in combination.

"Stereoisomers" are compounds, which have identical chemical constitution, but differ with regard to the arrangement of the atoms or groups in space.

A "diastereomer" is a stereoisomer with two or more centers of chirality and whose molecules are not mirror images of one another. Diastereomers have different physical properties, e.g., melting points, boiling points, spectral properties, and reactivities. Mixtures of diastereomers may separate under high resolution analytical procedures such as electrophoresis, crystallization in the presence of a resolving agent, or chromatography, using, for example a chiral HPLC column.

"Enantiomers" refer to two stereoisomers of a compound, which are non-superimposable mirror images of one another. A 50:50 mixture of enantiomers is referred to as a racemic mixture or a racemate, which may occur where there has been no stereoselection or stereospecificity in a chemical reaction or process.

"Pharmaceutically acceptable salts" include derivatives of the disclosed compounds in which the parent compound is modified by making inorganic and organic, non-toxic, acid or base addition salts thereof. The salts of the present compounds can be synthesized from a parent compound that contains a basic or acidic moiety by conventional chemical methods. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Generally, non-aqueous media such as ether, ethyl acetate, ethanol, isopropanol, or acetonitrile are used, where practicable. Salts of the present compounds further include solvates of the compounds and of the compound salts.

Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts and the quaternary ammonium salts of the parent compound formed, for example, from non-toxic inorganic or organic acids. For example, conventional non-toxic acid salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, HOOC—$(CH_2)_n$—COOH where n is 0-4, and the like. Lists of additional suitable salts may be found, e.g., in *Remington's Pharmaceutical Sciences,* 17th ed., Mack Publishing Company, Easton, Pa., p. 1418 (1985).

"Pharmaceutical compositions" means compositions comprising at least one active agent, such as a compound or salt of a formula described herein, and at least one other substance, such as a carrier. Pharmaceutical compositions meet the U.S. FDA's GMP (good manufacturing practice) standards for human or non-human drugs.

"Carrier" means a diluent, excipient, or vehicle with which an active compound is administered. A "pharmaceutically acceptable carrier" means a substance, e.g., excipient, diluent, or vehicle, that is useful in preparing a pharmaceutical composition that is generally safe, non-toxic and neither biologically nor otherwise undesirable, and includes a carrier that is acceptable for veterinary use as well as human pharmaceutical use. A "pharmaceutically acceptable carrier" includes both one and more than one such carrier.

"Cell proliferative disorders" refer to disorders wherein unwanted cell proliferation of one or more subset(s) of cells in a multicellular organism occurs, resulting in harm, for example, pain or decreased life expectancy to the organism. Cell proliferative disorders include, but are not limited to, tumors, benign tumors, blood vessel proliferative disorders, autoimmune disorders, and fibrotic disorders.

A "subject" is a human or non-human animal provided a compound as described herein. "Subject" includes a patient, wherein a patient is a human or non-human animal in need of medical treatment. Medical treatment can include treatment of an existing condition, such as a disease or disorder, prophylactic or preventative treatment, or diagnostic treatment. In some embodiments the patient is a human patient. In certain embodiments treatment is treatment of an existing condition.

"Providing" means giving, administering, selling, distributing, transferring (for profit or not), manufacturing, compounding, or dispensing.

"Inhibiting p97 and/or inducing ER stress" includes effecting any significant inhibition of p97 activity or affecting any significant indicia of ER stress. P97 Inhibition and/or ER stress induction may be observed directly or indirectly. For example p97 Inhibition and/or ER stress induction includes amelioration of the symptoms of a disease or disorder in which p97 activity or ER stress is implicated is included. Such diseases and disorders include cell proliferative disorders, particularly cancer, and viral infections. P97 Inhibition and/or ER stress induction also includes increases in markers ATF3 and ATF4, upregulation of NOXA protein level, accumulation of polyubiquitinated proteins, and downregulation of ubiquitinated histone H2A (upper band in H2A immunoblot).

"Treatment" or "treating" means providing an active compound to a patient in an amount sufficient to measurably reduce any symptom of a disease or disorder responsive to p97 inhibition and/or ER stress induction. The disease or disorder responsive to p97 inhibition and/or ER stress induction can be, e.g., a disorder associated with undesired cell proliferation such as a cancer or a viral infection. Cancers for treatment include both solid and disseminated cancers, for example multiple myeloma and mantle cell lymphoma (MCL), chronic lymphocytic leukemia (CLL), T-cell leukemia, multiple myeloma, Burkitt's lymphoma, retinoblastoma, osteosarcoma, breast cancer, bladder cancer, prostate cancer, renal carcinoma, small-cell lung cancer, and a cancer associated with viral infections, such as a cervical cancer associated with human papilloma virus. Viral infections include cytomegalovirus and retroviral infections, for example human immunodeficiency virus (HIV) infection.

A "therapeutically effective amount" of a pharmaceutical composition means an amount effective, when administered to a patient, to provide a therapeutic benefit such as an amelioration of symptoms, e.g., an amount effective to decrease the symptoms of a disease or disorder.

A significant change is any detectable change that is statistically significant in a standard parametric test of statistical significance such as Student's T-test, where p<0.05.

Chemical Description

In addition to methods of treatment employing compounds of Formula I or II, presented in the SUMMARY section, included herein is a method of treating disorders responsive to p97 inhibition and/or ER stress induction a viral infection in a patient comprising providing a therapeutically effective amount of a compound or pharmaceutically acceptable salt thereof of Formula III or Formula IV (both subformulae of Formula I).

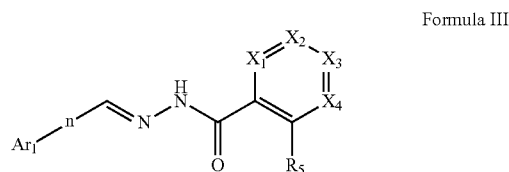

Formula III

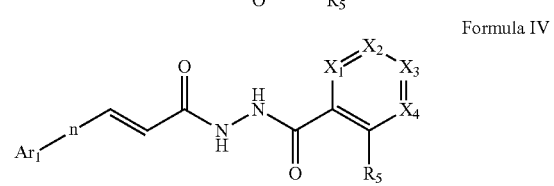

Formula IV

Further included are biosteres of Formula I, in which the amide or diamide is replaced by an amide biostere, such as alpha-trifluoromethyl-amine. For example, Formula V, VI, and VII.

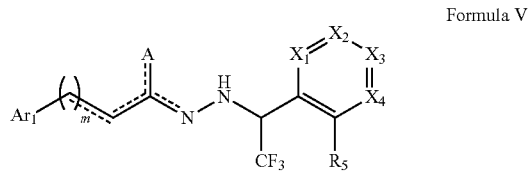

Formula V

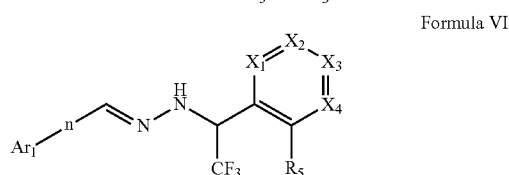

Formula VI

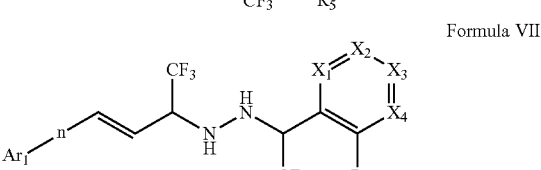

Formula VII

In Formulas V, VI, and VII all variables carry the definitions set forth for Formula I or any of the definitions set forth below, with the exception of A in Formula V which may be hydrogen, oxo, or $CF_3$.

Within Formula I-VII the variables, e.g. $Ar_1$, n, $X_1$-$X_4$, and $R_5$, carry the following definitions.

$Ar_1$ is furanyl, thienyl, pyridyl, or phenyl, each of which is optionally substituted with one or more substituents independently chosen from halogen, hydroxyl, amino, cyano, nitro, —CHO, —COOH, —$PO_4$, $C_1$-$C_4$alkyl, $C_1$-$C_4$alkoxy, $C_2$-$C_4$alkanoyl, $C_1$-$C_4$alkylester, mono- and di-($C_1$-$C_4$)alkylamino, $C_1$-$C_2$haloalkyl, and $C_1$-$C_2$haloalkoxy.

n is a bond or n is a 1 to 4 carbon alkylene or alkenylene linker;

$X_1$ is $CR_1$ or N; $X_2$ is $CR_2$ or N; $X_3$ is $CR_3$ or N; and $X_4$ is $CR_4$ or N; wherein no more than 2 of $X_1$-$X_4$ are N.

$R_1$ to $R_4$ are independently chosen from hydrogen, halogen, hydroxyl, amino, cyano, nitro, $C_1$-$C_4$alkyl, $C_1$-$C_4$alkoxy, mono- and di-($C_1$-$C_4$)alkylamino, $C_1$-$C_2$haloalkyl, and $C_1$-$C_2$haloalkoxy.

$R_5$ is hydrogen, halogen, hydroxyl, amino, cyano, nitro, $C_1$-$C_4$alkyl, $C_1$-$C_4$alkoxy, mono- or di-($C_1$-$C_4$)alkylamino, $C_1$-$C_2$haloalkyl, or $C_1$-$C_2$haloalkoxy.

One of the following conditions may be present:

$R_1$ and $R_2$ are taken together to form a 6-membered carbocyclic ring, or a 5- or 6-membered heterocyclic ring containing 1 or 2 heteroatoms independently chosen from N, O, and S, which carbocyclic or heterocyclic $R_1$/$R_2$ ring is substituted with 0 or 1 or more substituents independently chosen from halogen, hydroxyl, amino, cyano, nitro, $C_1$-$C_4$alkyl, $C_1$-$C_4$alkoxy, mono- and di-($C_1$-$C_4$)alkylamino, $C_1$-$C_2$haloalkyl, and $C_1$-$C_2$haloalkoxy.

$R_2$ and $R_3$ are taken together to form a 6-membered carbocyclic ring, or a 5- or 6-membered heterocyclic ring containing 1 or 2 heteroatoms independently chosen from N, O, and S, which carbocyclic or heterocyclic $R_2$/$R_3$ ring is substituted with 0 or 1 or more substituents independently chosen from halogen, hydroxyl, amino, cyano, nitro, $C_1$-$C_4$alkyl, $C_1$-$C_4$alkoxy, mono- and di-($C_1$-$C_4$)alkylamino, $C_1$-$C_2$haloalkyl, and $C_1$-$C_2$haloalkoxy.

($R_3$ and $R_4$ are taken together to form a 6-membered carbocyclic ring, or a 5- or 6-membered heterocyclic ring containing 1 or 2 heteroatoms independently chosen from N, O, and S, which carbocyclic or heterocyclic $R_3$/$R_4$ ring is substituted with 0 or 1 or more substituents independently chosen from halogen, hydroxyl, amino, cyano, nitro, $C_1$-$C_4$alkyl, $C_1$-$C_4$alkoxy, mono- and di-($C_1$-$C_4$)alkylamino, $C_1$-$C_2$haloalkyl, and $C_1$-$C_2$haloalkoxy; or $R_1$ and $R_2$ are taken together to form a 6-membered carbocyclic ring, or a 5- or 6-membered heterocyclic ring containing 1 or 2 heteroatoms independently chosen from N, O, and S, and $R_4$ and $R_5$ are taken together to form a 6-membered carbocyclic ring, or a 5- or 6-membered heterocyclic ring containing 1 or 2 heteroatoms independently chosen from N, O, and S, thereby forming a three ring system; which three ring system is substituted with 0 or 1 or more substituents independently chosen from halogen, hydroxyl, amino, cyano, nitro, $C_1$-$C_4$alkyl. For example the three ring system may be an optionally substituted anthracene.

Other methods of treating a disease or disorder responsive to p97 inhibition and/or ER stress induction or a viral infection in a patient include administering compounds and salts thereof as follows:

(a) Formula VIII and Formula IX, in which the variables $A_1$, $X_1$-$X_4$, and $R_5$ carry the definitions set forth above.

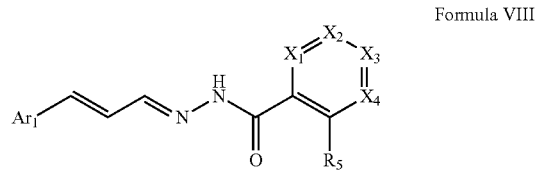

Formula VIII

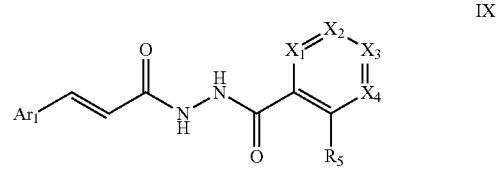

IX (b) Compounds of Formula I-IX in which $Ar_1$ is a 2-furanyl or phenyl, each of which is substituted with at least one nitro, hydroxyl, amino, —CHO, —COOH, or —$PO_4$ substituent and optionally substituted with one or more substituents independently chosen from cyano, $C_1$-$C_2$alkyl, $C_1$-$C_2$alkoxy, mono- and di-($C_1$-$C_2$)alkylamino, and $C_1$-$C_2$haloalkoxy.

(c) Compounds of Formula X and XI

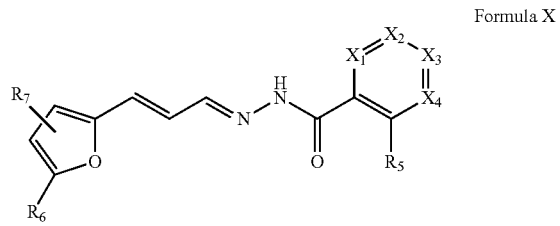

Formula X

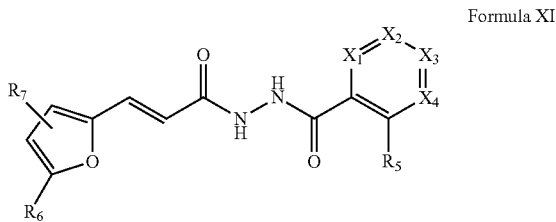

Formula XI wherein $R_6$ is nitro, cyano, —CHO, —COOH, or —$PO_4$; and $R_7$ is 0, 1, or 2 substituents independently chosen from halogen, $C_1$-$C_2$alkyl, and $C_1$-$C_2$alkoxy.

(d) Also included are compounds and salts of Formula X and XI in which $R_6$ is nitro and $R_7$ absent.

(e) Compounds and salts of Formula I to XI wherein

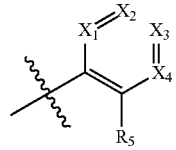

is a phenyl, naphthyl, quinolinyl, isoquinolinyl, or pyridyl, in which $R_5$ is hydrogen, halogen, hydroxyl, amino, cyano, nitro, $C_1$-$C_4$alkyl, $C_1$-$C_4$alkoxy, mono- or di-($C_1$-$C_4$)alkylamino, $C_1$-$C_2$haloalkyl, or $C_1$-$C_2$haloalkoxy.

Each of which phenyl, naphthyl, quinolinyl, isoquinolinyl, is substituted with 0, 1, or 2 substituents independently chosen from halogen, hydroxyl, amino, cyano, nitro, $C_1$-$C_4$alkyl, $C_1$-$C_4$alkoxy, mono- and di-$(C_1$-$C_4)$alkylamino, $C_1$-$C_2$haloalkyl, and $C_1$-$C_2$haloalkoxy.

(f) Compounds and salts of Formula I to XI wherein

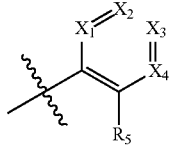

is a phenyl, naphthyl, quinolinyl, isoquinolinyl, or pyridyl, in which $R_5$ is hydrogen or hydroxyl. Each of which phenyl, naphthyl, quinolinyl, isoquinolinyl, is substituted with 0, 1, or 2 substituents independently chosen from chloro, bromo, hydroxyl, nitro, methyl, methoxy, and trifluoromethyl.

(g) Compounds and salts of Formula I to XI, wherein

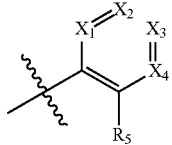

is phenyl, 3-pyridyl, 2-, 3-, or 4-hydroxy phenyl, 3-hydroxy-naphth-2-yl, 1-hydroxy-isoquinolin-3-yl, 4-hydroxy-quinolin-3-yl; each of which is additionally substituted with 0, 1, or 2 substituents independently chosen from hydroxyl, nitro, chloro, bromo, methyl, methoxy, and trifluoromethyl.

(h) Compounds and salts of Formula I to XI, wherein

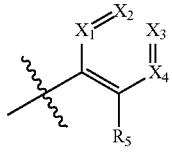

is 3-hydroxy-naphth-2-yl.

(i) Compounds and salts of Formula I to XI in which $Ar_1$ is nitro-phenyl or nitro-furanyl.

(j) Compounds and salts of Formula I to XI in which $Ar_1$ is

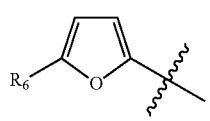

and $R_6$ is nitro, cyano, —$PO_4$, —CHO, or —COOH. In certain embodiments $R_6$ is nitro.

Also provided herein are compounds and pharmaceutically acceptable salts of Formula IV and V (shown above) in which the variables $Ar_1$, $X_1$-$X_4$, and $R_5$ are defined as follows.

$Ar_1$ is

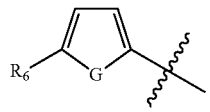

where G is O, N, or S, and $R_6$ is nitro, cyano, —$PO_4$, —CHO, or —COOH.

$X_1$ is $CR_1$ or N; $X_2$ is $CR_2$ or N; $X_3$ is $CR_3$ or N; $X_4$ is $CR_4$ or N;
wherein

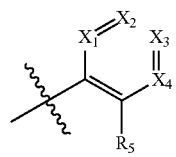

is not unsubstituted or substituted phenyl, unsubstituted pyridyl, or unsubstituted pyridizine, or 2-methylbenzo[d]thiazole, and no more than 2 of $X_1$-$X_4$ are N.

$R_1$ to $R_4$ are independently chosen from hydrogen, halogen, hydroxyl, amino, cyano, nitro, $C_1$-$C_4$alkyl, $C_1$-$C_4$alkoxy, mono- and di-$(C_1$-$C_4)$alkylamino, $C_1$-$C_2$haloalkyl, and $C_1$-$C_2$haloalkoxy.

$R_5$ is hydrogen, halogen, hydroxyl, amino, cyano, nitro, $C_1$-$C_4$alkyl, $C_1$-$C_4$alkoxy, mono- or di-$(C_1$-$C_4)$alkylamino, $C_1$-$C_2$haloalkyl, or $C_1$-$C_2$haloalkoxy.

One of the following two conditions may be present.

$R_2$ and $R_3$ may be taken together to form a 6-membered carbocyclic ring, or a 5- or 6-membered heterocyclic ring containing 1 or 2 heteroatoms independently chosen from N, O, and S, which carbocyclic or heterocyclic $R_2$/$R_3$ ring is substituted with 0 or 1 or more substituents independently chosen from halogen, hydroxyl, amino, cyano, nitro, $C_1$-$C_4$alkyl, $C_1$-$C_4$alkoxy, mono- and di-$(C_1$-$C_4)$alkylamino, $C_1$-$C_2$haloalkyl, and $C_1$-$C_2$haloalkoxy;

$R_3$ and $R_4$ may be taken together to form a 6-membered carbocyclic ring, or a 5- or 6-membered heterocyclic ring containing 1 or 2 heteroatoms independently chosen from N, O, and S, which carbocyclic or heterocyclic $R_3$/$R_4$ ring is substituted with 0 or 1 or more substituents independently chosen from halogen, hydroxyl, amino, cyano, nitro, $C_1$-$C_4$alkyl, $C_1$-$C_4$alkoxy, mono- and di-$(C_1$-$C_4)$alkylamino, $C_1$-$C_2$haloalkyl, and $C_1$-$C_2$haloalkoxy.

Further included are compounds and salts of Formula X and XI as described above in which any of the following conditions are met.

(k) $Ar_1$ is

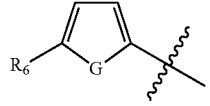

where $R_6$ is nitro and G is oxygen.

(l) $R_1$ to $R_4$ are independently chosen from hydrogen, halogen, hydroxyl, nitro, $C_1$-$C_2$alkyl, $C_1$-$C_2$alkoxy, mono- or di-$(C_1$-$C_2)$alkylamino, trifluoromethyl, and trifluoromethoxy.

$R_5$ is hydrogen or hydroxyl.

Additionally one of the following two conditions is present:

(1) $R_2$ and $R_3$ are taken together to form a 6-membered aromatic ring or 6-membered heteroaromatic ring containing one or two nitrogen atoms, which 6-membered $R_2/R_3$ ring is substituted with 0 or 1 or more substituents independently chosen from halogen, hydroxyl, nitro, $C_1$-$C_2$alkyl, $C_1$-$C_2$alkoxy, mono- and di-($C_1$-$C_2$)alkylamino, trifluoromethyl, and trifluoromethoxy.

(2) $R_3$ and $R_4$ are taken together to form a 6-membered aromatic ring or 6-membered heteroaromatic ring containing one or two nitrogen atoms, which 6-membered $R_3/R_4$ ring is substituted with 0 or 1 or more substituents independently chosen from halogen, hydroxyl, nitro, $C_1$-$C_2$alkyl, $C_1$-$C_2$alkoxy, mono- and di-($C_1$-$C_2$)alkylamino, trifluoromethyl, and trifluoromethoxy.

(m) $X_1$ is $CR_1$, $X_4$ is $CR_4$; $R_5$ is hydroxyl; $X_2$ is $CR_2$; and $X_3$ is $CR_3$. $R_2$ and $R_3$ are taken together to form a 6-membered aromatic ring, which 6-membered $R_2/R_3$ ring is substituted with 0 or 1 or more substituents independently chosen from halogen, hydroxyl, nitro, $C_1$-$C_2$alkyl, $C_1$-$C_2$alkoxy, mono- and di-($C_1$-$C_2$)alkylamino, trifluoromethyl, and trifluoromethoxy. That is

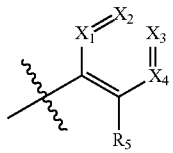

is a group of the formula

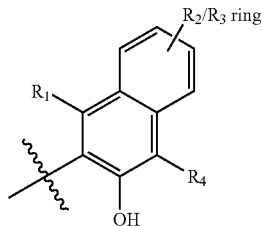

(n) $X_1$ is N; $X_2$ is $CR_2$; $R_5$ is hydroxyl; and $X_3$ is $CR_3$; $X_4$ is $CR_4$; and $X_3$ and $X_4$ are taken together to form a 6-membered aromatic ring, which 6-membered $R_3/R_4$ ring is substituted with 0 or 1 or more substituents independently chosen from halogen, hydroxyl, nitro, $C_1$-$C_2$alkyl, $C_1$-$C_2$alkoxy, mono- and di-($C_1$-$C_2$)alkylamino, trifluoromethyl, and trifluoromethoxy. That is

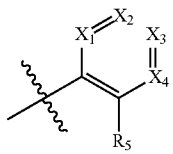

is a group of the formula

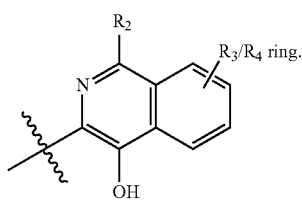

(o) $X_1$ is $CR_1$; $X_2$ is N; $R_5$ hydroxyl; and $X_3$ is $CR_3$; $X_4$ is $CR_4$; and $X_3$ and $X_4$ are taken together to form a 6-membered aromatic ring, which 6-membered $R_3/R_4$ ring is substituted with 0 or 1 or more substituents independently chosen from halogen, hydroxyl, nitro, $C_1$-$C_2$alkyl, $C_1$-$C_2$alkoxy, mono- and di-($C_1$-$C_2$)alkylamino, trifluoromethyl, and trifluoromethoxy.
That is

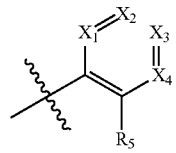

is a group of the formula

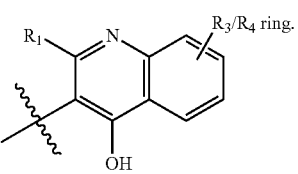

Any of the conditions set forth above for compounds of Formula I to Formula VII may be combined so long as a stable compound results, for example included herein are compounds of Formula II in which

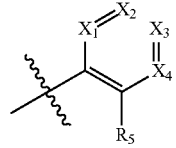

is phenyl, 3-pyridyl, 2-, 3-, or 4-hydroxy phenyl, 3-hydroxynaphth-2-yl, 1-hydroxy and $R_5$ is hydrogen or hydroxyl.

In addition to compounds and salts of Formula I-XI shown above compounds and salts of Formula XII and XIII are also provided.

Formula XII

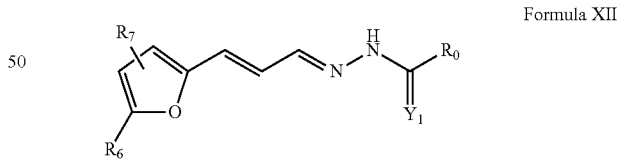

Formula XIII

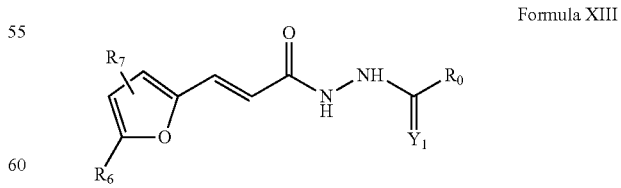

In Formula XII and XIII the variables $R_6$ and $R_7$ may have any of the definitions set forth herein for these variables. $Y_1$ is S, O or N, and $R_o$ is amino, $C_1$-$C_4$alkyl, $C_1$-$C_4$alkoxy, or mono-, di-, or tri-(quarternized)$C_1$-$C_4$alkylamino($C_0$-$C_2$alkyl).

Pharmaceutical Preparations

The hydrazone and diacyl hydrazine compounds can be administered as the neat chemical, but are specifically administered as a pharmaceutical composition, for example a pharmaceutical formulation comprising a hydrazone or a diacyl hydrazine compound of Formula I or pharmaceutically acceptable salt thereof, together with at least one pharmaceutically acceptable carrier. The pharmaceutical composition can be is formulated as an injectable fluid, an aerosol, a cream, a gel, a tablet, a pill, a capsule, a syrup, or a transdermal patch.

The hydrazone and diacyl hydrazine compounds may be administered orally, topically, parenterally, by inhalation or spray, sublingually, transdermally, via buccal administration, rectally, as an ophthalmic solution, or by other means, in dosage unit formulations containing conventional pharmaceutically acceptable carriers. The pharmaceutical composition may be formulated as any pharmaceutically useful form, e.g., as an aerosol, a cream, a gel, a pill, a capsule, a tablet, a syrup, a transdermal patch, or an ophthalmic solution. Some dosage forms, such as tablets and capsules, are subdivided into suitably sized unit doses containing appropriate quantities of the active components, e.g., an effective amount to achieve the desired purpose.

Carriers include excipients and diluents and must be of sufficiently high purity and sufficiently low toxicity to render them suitable for administration to the patient being treated. The carrier can be inert or it can possess pharmaceutical benefits of its own. The amount of carrier employed in conjunction with the compound is sufficient to provide a practical quantity of material for administration per unit dose of the compound.

Classes of carriers include, but are not limited to binders, buffering agents, coloring agents, diluents, disintegrants, emulsifiers, flavorings, glidants, lubricants, preservatives, stabilizers, surfactants, tableting agents, and wetting agents. Some carriers may be listed in more than one class, for example vegetable oil may be used as a lubricant in some formulations and a diluent in others. Exemplary pharmaceutically acceptable carriers include sugars, starches, celluloses, powdered tragacanth, malt, gelatin, talc, and vegetable oils. Optional active and/or inactive agents may be included in the pharmaceutical compositions, provided that such agents do not substantially interfere with the activity of the hydrazone and diacyl hydrazine compounds used in the pharmaceutical compositions. The optional active is an additional active agent that is not a compound or salt of Formula I.

The pharmaceutical compositions can be formulated for oral administration. These compositions contain between 0.1 and 99 weight % (wt. %) of a hydrazone or a diacyl hydrazine compound and usually at least about 5 wt. % of a hydrazone or a diacyl hydrazine compound. Some embodiments contain from about 25 wt. % to about 50 wt. % or from about 5 wt. % to about 75 wt. % of the hydrazone or diacyl hydrazine compound.

Targeting Methods

It has been discovered that certain compounds provided herein act as ER membrane targeting agents. That is these compounds specifically concentrate in the ER membrane. When bound to a second active agent, such as an ER stress inducer, either covalently or non-covalently, the ER membrane targeting agents provided herein will concentrate the second active agent in the ER. This effect is demonstrated in FIG. 2, which shows localization of EERI in the membrane. EERI is constituted of 5138380 covalently modified with 5-nitrofuryl-acrolein, which produces a fluorescent signal. EERI is accumulated in a perinuclear compartment, whereas 5-nitrofuryl-acrolein displays a ubiquitous localization in cells. The compound 5138380 produces no fluorescence signal from the cells. An asterisk indicates a potential point of attachment for a second active agent. In certain embodiments the second active agent will be a cancer drug known to exhibit activity through targeting molecules localized in the ER membrane. Such drugs include but are not limited to cisplatin, bortezomib, thapsigargin, Bcl family antagonist, inhibitors of ER membrane bound kinases Ire1 and PERK et al.

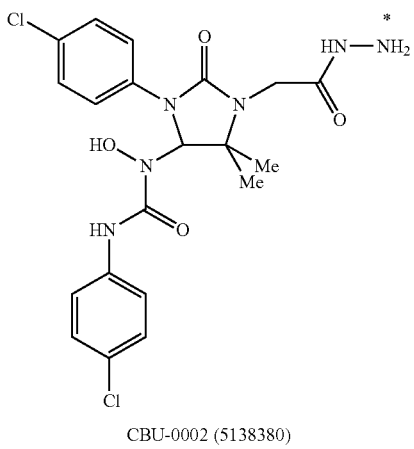

CBU-0002 (5138380)

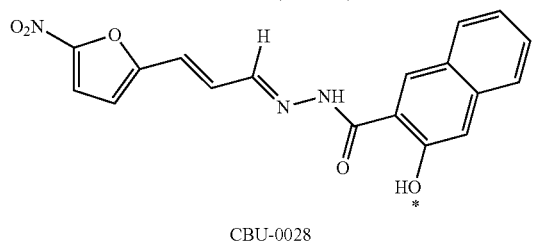

CBU-0028

Treatment Methods

The compounds of Formula I or a salt thereof, as well as pharmaceutical compositions comprising the compounds, are useful for treating a disease or disorder responsive to p97 inhibition and/or ER stress induction in a patient. The method of treating a disease or disorder responsive to p97 inhibition and/or ER stress induction in a patient comprises providing to the patient an effective amount of a compound of Formula I: In an embodiment the patient is a mammal, specifically a primate, more specifically a human. An effective amount of a pharmaceutical composition may be an amount sufficient to inhibit the progression of a disease or disorder; or cause a regression of a disease or disorder.

An effective amount of a compound or pharmaceutical composition described herein will also provide a sufficient concentration of a hydrazone or diacyl hydrazine compound when administered to a patient. A sufficient concentration is a concentration of the compound in the patient's body necessary to prevent or combat the disorder. Such an amount may be ascertained experimentally, for example by assaying blood concentration of the compound, or theoretically, by calculating bioavailability.

Methods of treatment include providing certain dosage amounts of a hydrazone or hydrazine derivative to a patient. Dosage levels of each compound of from about 0.1 mg to about 140 mg per kilogram of body weight per day are useful in the treatment of the above-indicated conditions (about 0.5 mg to about 7 g per patient per day). The amount of compound that may be combined with the carrier materials to produce a single dosage form will vary depending upon the patient treated and the particular mode of administration. Dosage unit forms will generally contain between from about 1 mg to about 500 mg of each active compound. In certain embodiments 25 mg to 500 mg, or 25 mg to 200 mg of a compound of Formula I are provided daily to a patient. Frequency of dosage may also vary depending on the compound used and the particular disease treated. However, for treatment of most diseases and disorders, a dosage regimen of 4 times daily or less can be used and in certain embodiments a dosage regimen of 1 or 2 times daily is used.

The compounds of Formula I may be used to treat diseases and disorders responsive to p97 inhibition and/or ER stress induction including disorders associated with undesired cell proliferation, for example cancer, and viral infections. In certain embodiments, the patient is suffering from a cell proliferative disorder or disease. The cell proliferative disorder can be cancer, tumor (cancerous or benign), neoplasm, neovascularization, vascularization, cardiovascular disease, intravasation, extravasation, arthritis, infection, Alzheimer's Disease, blood clot, atherosclerosis, melanoma, skin disorder, rheumatoid arthritis, diabetic retinopathy, macular edema, or macular degeneration, inflammatory and arthritic disease, or autoimmune disease. Cancers for treatment include both solid and disseminated cancers. Exemplary solid cancers (tumors) that may be treated by the methods provided herein include e.g. cancers of the lung, prostate, breast, liver, colon, breast, kidney, pancreas, brain, skin including malignant melanoma and Kaposi's sarcoma, testes or ovaries, carcinoma, and sarcoma. Exemplary disseminated cancers include leukemias or lymphoma including Hodgkin's disease, multiple myeloma and mantle cell lymphoma (MCL), chronic lymphocytic leukemia (CLL), T-cell leukemia, multiple myeloma, and Burkitt's lymphoma. Exemplary autoimmune diseases include, but are not limited to lupus. Viral infections include cytomegalovirus and retroviral infections, for example human immunodeficiency virus (HIV) infection.

Particularly included herein are methods of treating cancer by providing a hydrazone or diacyl hydrazine compound to a patient wherein the cancer is a solid tumor or disseminated cancer.

Further included are methods of treating cancer by providing a hydrazone or diacyl hydrazine, or related compound to a patient wherein the cancer is leukemia, multiple myeloma or lymphoma.

Also included herein are methods of treating a patient for a disease or disorder responsive to p97 inhibition and/or ER stress induction, including cancer, wherein the patient is resistant to treatment with a proteasome inhibitor. In certain embodiments the proteasome inhibitor to which the patient is resistant is bortezomib.

Also included are methods of treating a patient for a disease or disorder responsive to p97 inhibition and/or ER stress induction, wherein the disorder is an autoimmune disorder and the autoimmune disorder is lupus.

Further provided are methods of treating a viral infection in a patient by providing a hydrazone or diacyl hydrazine compound to the patient, wherein the viral infection is a retroviral infection, including methods in which the viral infection is HIV.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

In an embodiment, the invention provides a method of treating cancer in a patient identified as in need of such treatment, the method comprising providing to the patient an effective amount of a compound of Formula I. In another aspect, the invention provides a method of treating a patient with a viral infection comprising providing to the patient an effective amount a compound of Formula I. Such administration decreases or eliminates the pool of infected cells and/or decreases the viral population.

One or more compounds of the invention including those of the formulae herein may be administered in coordination with a regime of one or more other chemotherapeutic agents, particularly a compound that functions against cancer cells other than by p97 inhibition and/or ER stress induction, such as an antineoplastic drug, e.g., an alkylating agent (e.g., mechloroethamine, chlorambucil, cyclophosamide, melphalan, or ifosfamide), an antimetabolite such as a folate antagonist (e.g., methotrexate), a purine antagonist (e.g. 6-mercaptopurine) or a pyrimidine antagonist (e.g., 5-fluorouracil). Other, non-limiting examples of chemotherapeutic agents that might be used in coordination with one or more compounds of the invention include taxanes and topoisomerase inhibitors. In addition, other non-limiting examples of active therapeutics include biological agents, such as monoclonal antibodies or IgG chimeric molecules, that achieve their therapeutic effect by specifically binding to a receptor or ligand in a signal transduction pathway associated with cancer (e.g. therapeutic antibodies directed against CD20 (e.g. rituximab) or against VEGF (e.g. bevacizumab)).

For an antiviral therapy, one or more compounds of Formula I may be administered in coordination with a regime of one or more other antiviral agents such as reverse transcriptase inhibitors such as dideoxynucleosides, e.g. zidovudine (AZT), 2',3'-dideoxyinosine (ddI) and 2',3'-dideoxycytidine (ddC), lamivudine (3TC), stavudine (d4T), and TRIZIVIR (abacavir+zidovudine+lamivudine), nonnucleosides, e.g., efavirenz (DMP-266, DuPont Pharmaceuticals/ Bristol Myers Squibb), nevirapine (Boehringer Ingleheim), and delaviridine (Pharmacia-Upjohn), TAT antagonists such as Ro 3-3335 and Ro 24-7429, protease inhibitors, e.g., indinavir (Merck), ritonavir (Abbott), saquinavir (Hoffmann LaRoche), nelfinavir (Agouron Pharmaceuticals), 141 W94 (Glaxo-Wellcome), atazanavir (Bristol Myers Squibb), amprenavir (GlaxoSmithKline), fosamprenavir (GlaxoSmithKline), tipranavir (Boehringer Ingleheim), KALETRA (lopinavir+ritonavir, Abbott), and other agents such as 9-(2-hydroxyethoxymethyl)guanine (acyclovir), interferon, e.g., alpha-interferon, interleukin II, and phosphonoformate (Foscarnet), or entry inhibitors, e.g., T20 (enfuvirtide, Roche/ Trimeris) or UK-427,857 (Pfizer), or in conjunction with other immune modulation agents or treatments including bone marrow or lymphocyte transplants or other medications such as levamisol or thymosin which would increase lymphocyte numbers and/or function as is appropriate. Because many of these drugs are directed to different targets, e.g., viral integration, a synergistic can result with this combination.

In an embodiment, one or more compounds of Formula I are used in conjunction with one or more therapeutic agents useful for treatment or prevention of HIV, a symptom associated with HIV infection, or other disease or disease symptom such as a secondary infection or an unusual tumor, such as herpes, cytomegalovirus, Kaposi's sarcoma and Epstein-Barr virus-related lymphomas among others, that can result in HIV immuno-compromised patients. In certain embodiments of the invention, one or more compounds of Formula I are used in conjunction with a standard HIV antiviral treatment regimens. Without being limited by theory, it is believed that this combination is advantageous in that the compound(s) of the formulae herein can activate latent HIV infected cells to replicate by stimulating lytic viral replication, thus making them susceptible to the co-administered standard HIV antiviral treatment regimens. In this manner, the latent or secondary reservoirs of HIV-infected cells are depleted through "controlled" activation (rather than serendipitous or uncontrolled activation), resulting in more complete elimination of infection. In another aspect, the treatment methods herein include administration of a so-called HIV-drug "cocktail" or combination therapy, wherein a combination of reverse transcriptase inhibitor(s) and HIV protease inhibitor(s) is co-administered.

The compounds of Formula I can also be used in a method of inhibiting p97 and its associated deubiquitination. A method of inhibiting p97 in a patient can comprise providing to the patient an effective amount of a compound of Formula I.

In another aspect methods of treating a disease or disorder responsive to p97 inhibition and/or ER stress induction in a patient include providing a compound of a hydrozone or diacyl hydrazine, including a compound or salt of Formula I, to a patient together with an additional pharmaceutically active agent. In certain embodiments the additional active agent is a proteosome inhibitor, such as bortezomib.

In still another aspect, the invention provides a method of modulating the function of p97 and its associated deubiquitinatinases in a cell, the method comprising the step of providing to the subject one or more compounds of Formula I in an amount and under conditions sufficient to modulate the function of p p97 and its associated deubiquitination. In one embodiment, the modulation is a blocking regulation.

In another aspect, the invention provides for the use of a hydrazone or diacyl hydrazine compound disclosed herein in the manufacture of a medicament for inhibiting or reducing cancer in a patient.

Methods of treatment provided herein are also useful for treatment of mammals other than humans, including for veterinary applications such as to treat horses and livestock e.g. cattle, sheep, cows, goats, swine and the like, and pets (companion animals) such as dogs and cats.

For diagnostic or research applications, a wide variety of mammals will be suitable subjects including rodents (e.g. mice, rats, hamsters), rabbits, primates and swine such as inbred pigs and the like. Additionally, for in vitro applications, such as in vitro diagnostic and research applications, body fluids (e.g., blood, plasma, serum, cellular interstitial fluid, saliva, feces and urine) and cell and tissue samples of the above subjects will be suitable for use.

Compounds of Formula I may be administered singularly (i.e., sole therapeutic agent of a regime) to treat or prevent diseases and conditions such as undesired cell proliferation and/or viral infection as disclosed herein. Compounds, as described herein, including hydrazones and diacyl hydrazines, also may be administered as a "cocktail" formulation, e.g. coordinated administration of one or more compounds of Formula I together with one or more other active agents.

EXAMPLES

Example 1

Synthesis of (E)-3-hydroxy-N'-((E)-3-(5-nitrofuran-2-yl)allylidene)-2-naphthohydrazide Acetic acid (3 mL) is added to a mixture of 3-Hydroxy-2-naphthoic acid hydrazide (100 mg, 0.50 mmol) and (E)-3-(5-nitrofuran-2-yl)acrylaldehyde (99 mg, 0.59 mmol) and the resulting mixture is stirred for 2 h (Note: Immediate precipitation of the yellowish hydrazone product is observed after which the reaction mixture is stirred for another 2 h for completion). The reaction mixture is then diluted with 50% ether/hexanes. The yellowish solid is filtered with suction, washed with 50% ether/hexanes (100 mL) and dried to furnish 172 mg (99%) of the desired product as a yellowish solid. m. p. 259° C. $^1$H NMR (DMSO) δ 12.00 (br s, 1H), 11.3 (br s, 1H), 8.42 (s, 1H), 8.25 (d, 1H, J=8.1 Hz), 7.91 (d, 1H, J=8.4 Hz), 7.86-7.66 (m, 2H), 7.58-7.45 (m, 1H), 7.42-7.29 (m, 1H), 7.32 (s, 1H) and 7.25-7.06 (m, 3H); $^{13}$C NMR (DMSO) δ 163.7, 154.8, 153.8, 151.4, 148.5, 135.9, 130.5, 130.4, 128.7, 128.3, 126.8, 125.8, 124.3, 123.8, 120.5, 115.4, 113.6 and 110.5.

Example 2

Synthesis of (E)-3-hydroxy-N'-(3-(5-nitrofuran-2-yl) acryloyl)-2-naphthohydrazide

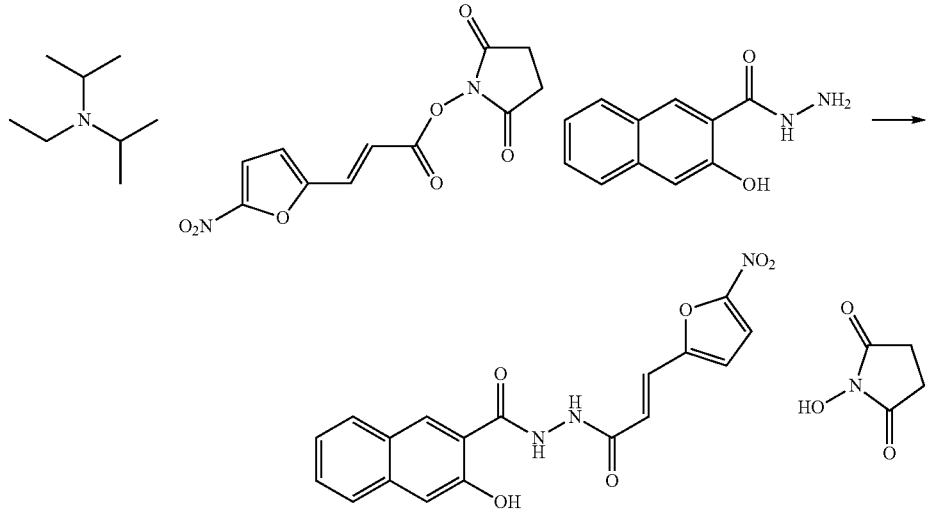

In a 25 mL round-bottomed flask the activated Nitro-furan ester (20 mg, 0.071 mmol) is dissolved in DMF (1 ml) to give a yellow suspension. Acyl-Hydrazine (14.43 mg, 0.071 mmol) and N,N-Diisopropylethylamine (0.025 ml, 0.143 mmol) are added and stirred at RT overnight.

The reaction mixture is diluted with water and 1N HCl is added until acidic pH (~1-2) is reached. The residue is filtered with suction. The solid is washed sequentially with water and ether, and dried under vacuum to provide 21 mg of CBU-062 as a pale yellow solid.

Example 3

Hydrazone and Diacyl Hydrazine Compounds

Table 1 contains exemplary hydrazone and diacyl hydrazine compounds prepared via the methods provided in Examples 1 and 2 and their cytotoxic activity.

TABLE I

| Compound | Structure | Name | IC50 |
|---|---|---|---|
| CBU-003 [EER1] | 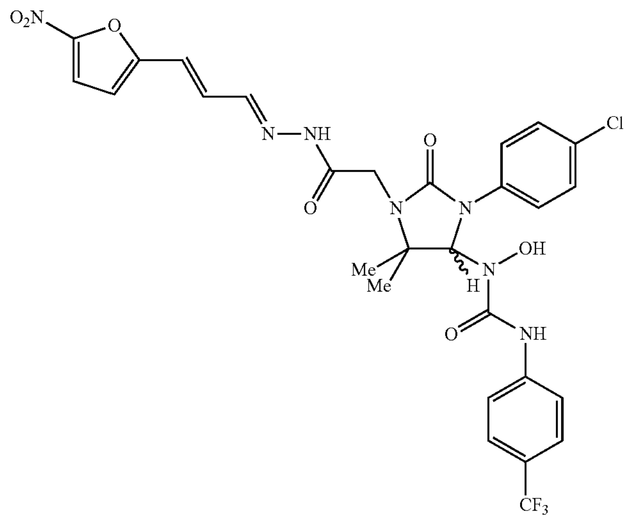 [SMILES: CC1(C)C(N(O)C(=O)Nc2ccc(C(F)(F)F)cc2)N(c2ccc(Cl)cc2)C(=O)N1CC(=O)N/N=C/C=C/c1ccc([N+](=O)[O-])o1] | | 3.5 |
| CBU-007 | 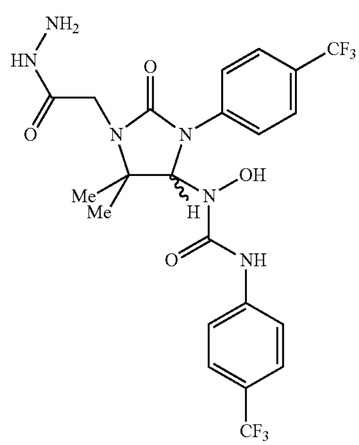 [SMILES: CC1(C)C(N(O)C(=O)Nc2ccc(C(F)(F)F)cc2)N(c2ccc(C(F)(F)F)cc2)C(=O)N1CC(=O)NN] | 1-(1-(2-hydrazinyl-2-oxoethyl)-5,5-dimethyl-2-oxo-3-(4-(trifluoromethyl)phenyl)imidazolidin-4-yl)-1-hydroxy-3-(4-(trifluoromethyl)phenyl)urea | 30 |

TABLE I-continued

| Compound | Structure | Name | IC50 |
|---|---|---|---|
| CBU-008 | 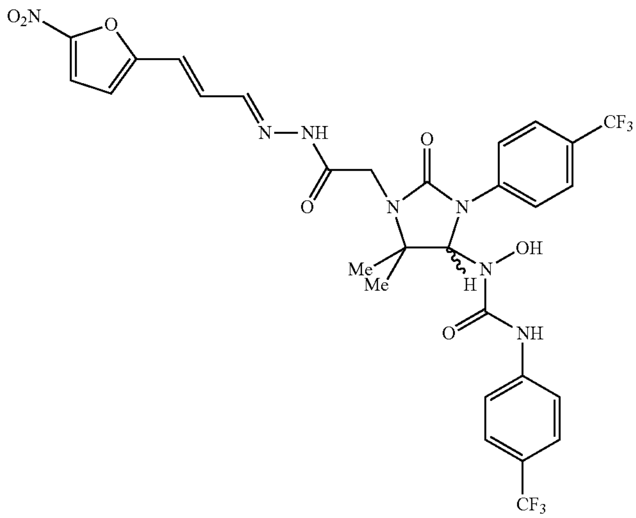 [SMILES: CC1(C)C(N(O)C(=O)Nc2ccc(C(F)(F)F)cc2)N(c2ccc(C(F)(F)F)cc2)C(=O)N1CC(=O)N/N=C/C=C/c1ccc([N+](=O)[O-])o1] | | 2.5 |
| CBU-013 | 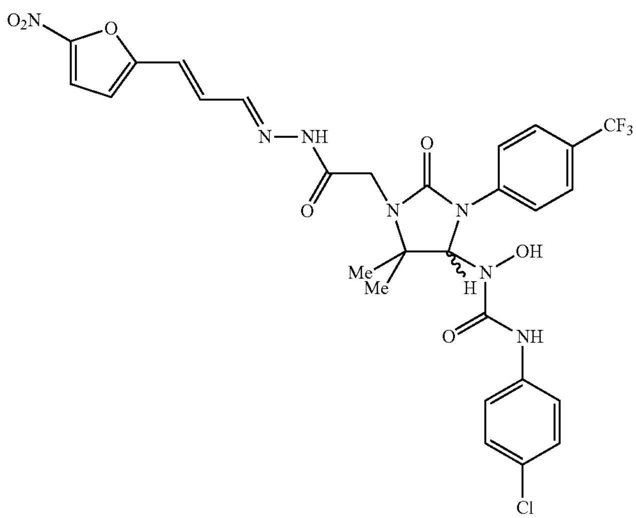 [SMILES: CC1(C)C(N(O)C(=O)Nc2ccc(Cl)cc2)N(c2ccc(C(F)(F)F)cc2)C(=O)N1CC(=O)N/N=C/C=C/c1ccc([N+](=O)[O-])o1] | | 3.0 |
| CBU-014 | 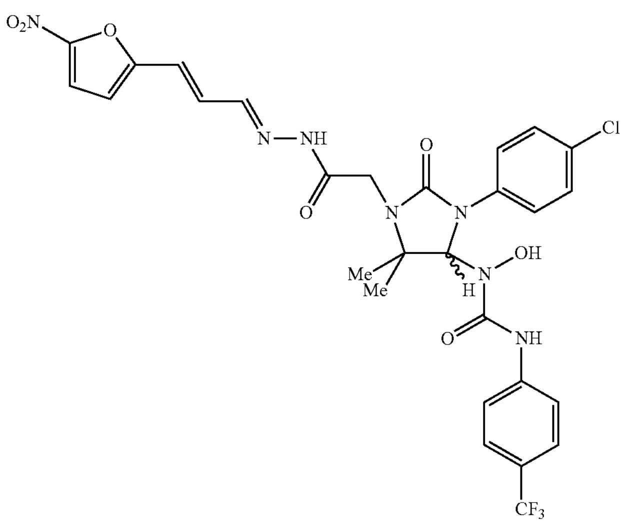 [SMILES: CC1(C)C(N(O)C(=O)Nc2ccc(C(F)(F)F)cc2)N(c2ccc(Cl)cc2)C(=O)N1CC(=O)N/N=C/C=C/c1ccc([N+](=O)[O-])o1] | | 3.0 |

TABLE I-continued

| Compound | Structure | Name | IC50 |
|---|---|---|---|
| CBU-015 | 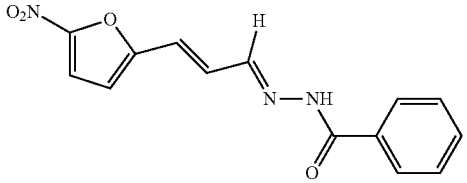 [SMILES: O=C(N/N=C/C=C/c1ccc([N+](=O)[O-])o1)c1ccccc1] | (E)-N'-((E)-3-(5-nitrofuran-2-yl)allylidene)benzohydrazide | 8.0 |
| CBU-016 | 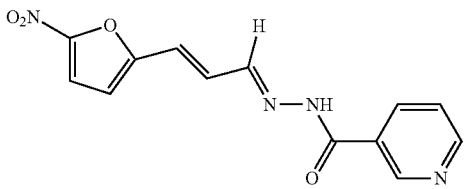 [SMILES: O=C(N/N=C/C=C/c1ccc([N+](=O)[O-])o1)c1cccnc1] | (E)-N'-((E)-3-(5-nitrofuran-2-yl)allylidene)nicotinonhydrazide | 7.0 |
| CBU-017 | 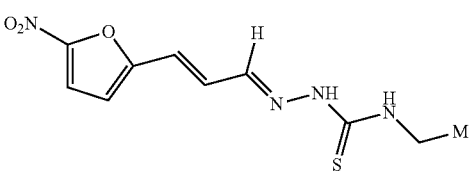 | (E)-N-ethyl-2-((E)-3-(5-nitrofuran-2-yl)allylidene)hydrazine-carbothioamide | 15.0 |
| CBU-018 | 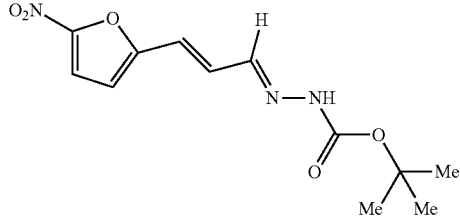 [SMILES: CC(C)(C)OC(=O)N/N=C/C=C/c1ccc([N+](=O)[O-])o1] | (E)-tert-butyl 2-((E)-3-(5-nitrofuran-2-yl)allylidene)hydrazine-carboxylate | 18.0 |
| CBU-019 | 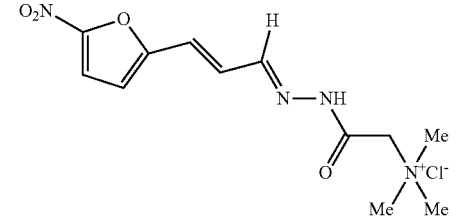 | | 3.5 |
| CBU-020 | 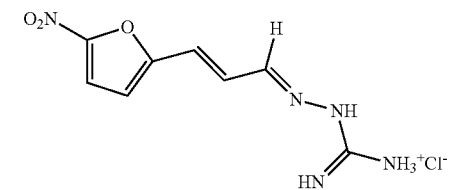 | (E)-2-((E)-3-(5-nitrofuran-2-yl)allylidene)hydrazine-carboximidamide hydrochloride | 4.0 |
| CBU-021 | 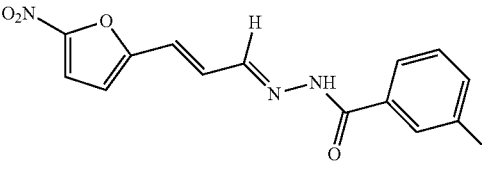 | (E)-3-hydroxy-N'-((E)-3-(5-nitrofuran-2-yl)allylidene)benzohydrazide | 8.0 |

TABLE I-continued

| Compound | Structure | Name | IC50 |
|---|---|---|---|
| CBU-022 | 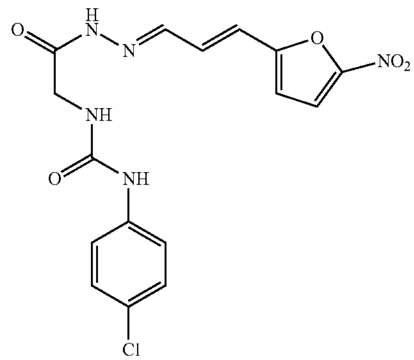 [SMILES: O=C(CNC(=O)Nc1ccc(Cl)cc1)N/N=C/C=C/c1ccc([N+](=O)[O-])o1] | 1-(4-chlorophenyl)-3-(2-((E)-2-((E)-3-(5-nitrofuran-2-yl)allylidene)hydrazinyl)-2-oxoethyl)urea | 6.0 |
| CBU-023 | 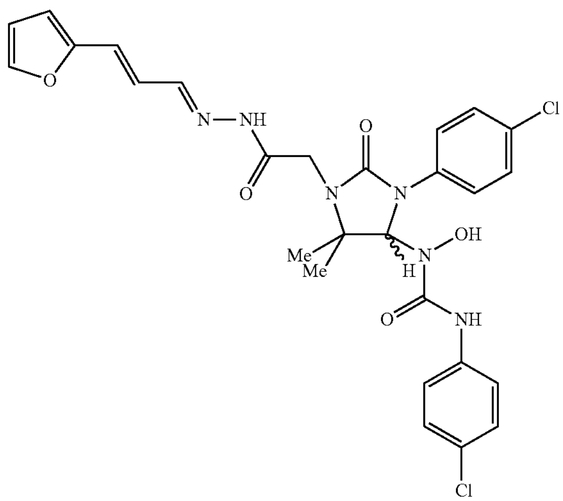 [SMILES: CC1(C)C(N(O)C(=O)Nc2ccc(Cl)cc2)N(c2ccc(Cl)cc2)C(=O)N1CC(=O)N/N=C/C=C/c1ccco1] | | 15.0 |
| CBU-024 | 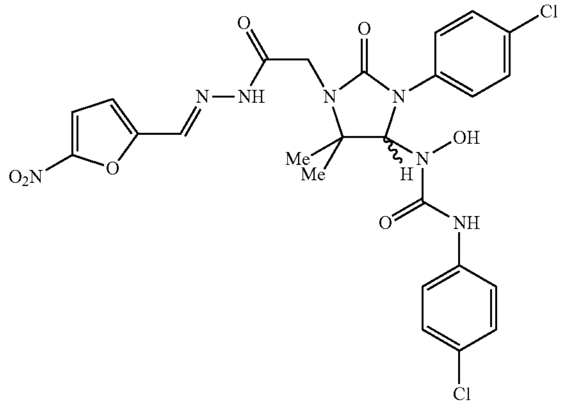 [SMILES: CC1(C)C(N(O)C(=O)Nc2ccc(Cl)cc2)N(c2ccc(Cl)cc2)C(=O)N1CC(=O)N/N=C/c1ccc([N+](=O)[O-])o1] | | 7.0 |
| CBU-025 | 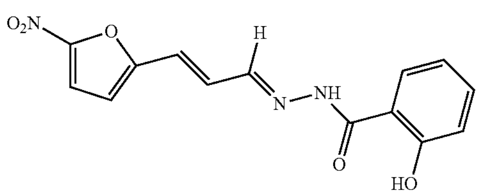 [SMILES: O=C(N/N=C/C=C/c1ccc([N+](=O)[O-])o1)c1ccccc1O] | (E)-2-hydroxy-N'-((E)-3-(5-nitrofuran-2-yl)allylidene)benzohydrazide | 6.5 |

TABLE I-continued

| Compound | Structure | Name | IC50 |
|---|---|---|---|
| CBU-027 | 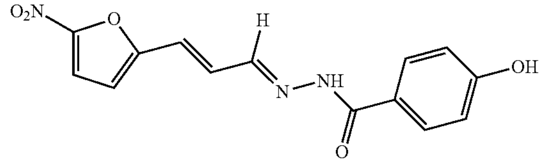 [SMILES: O=C(N/N=C/C=C/c1ccc([N+](=O)[O-])o1)c1ccc(O)cc1] | (E)-4-hydroxy-N'-((E)-3-(5-nitrofuran-2-yl)allylidene)benzohydrazide | 7.5 |
| CBU-028 | 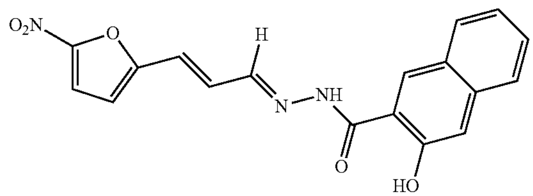 [SMILES: O=C(N/N=C/C=C/c1ccc([N+](=O)[O-])o1)c1cc2ccccc2cc1O] | (E)-3-hydroxy-N'-((E)-3-(5-nitrofuran-2-yl)allylidene)-2-naphthohydrazide | 3.0 |
| CBU-032 | 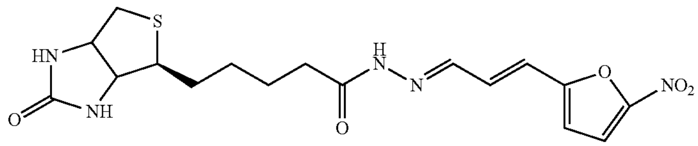 [SMILES: O=C(CCCC[C@@H]1SCC2NC(=O)NC21)N/N=C/C=C/c1ccc([N+](=O)[O-])o1] | (E)-N'-((E)-3-(5-nitrofuran-2-yl)allylidene)-5-((4S)-2-oxohexahydro-1H-thieno[3,4-d]imidazol-4-yl)pentanehydrazide | 25.0 |
| CBU-033 | 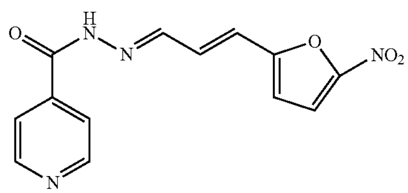 [SMILES: O=C(N/N=C/C=C/c1ccc([N+](=O)[O-])o1)c1ccncc1] | (E)-N'-((E)-3-(5-nitrofuran-2-yl)allylidene)isonicotinohydrazide | 6.0 |
| CBU-034 | 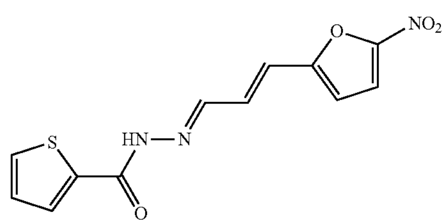 [SMILES: O=C(N/N=C/C=C/c1ccc([N+](=O)[O-])o1)c1cccs1] | (E)-N'-((E)-3-(5-nitrofuran-2-yl)allylidene)thiophene-2-carbohydrazide | 20.0 |
| CBU-036 | 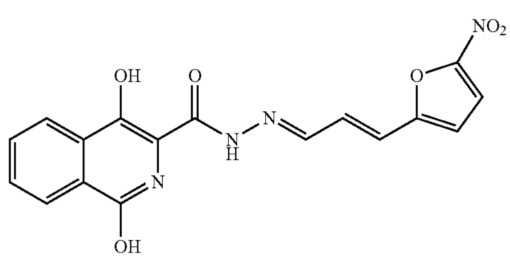 [SMILES: O=C(N/N=C/C=C/c1ccc([N+](=O)[O-])o1)c1nc(O)c2ccccc2c1O] | (E)-1,4-dihydroxy-N'-((E)-3-(5-nitrofuran-2-yl)allylidene)isoquinoline-3-carbohydrazide | 9.0 |
| CBU-038 | 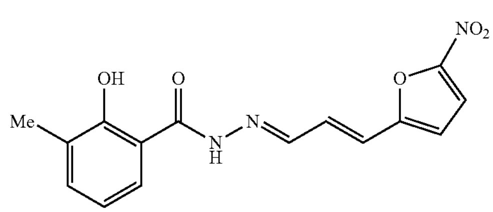 [SMILES: Cc1cccc(C(=O)N/N=C/C=C/c2ccc([N+](=O)[O-])o2)c1O] | (E)-2-hydroxy-3-methyl-N'-((E)-3-(5-nitrofuran-2-yl)allylidene)benzohydrazide | 9.0 |

TABLE I-continued

| Compound | Structure | Name | IC50 |
|---|---|---|---|
| CBU-039 | 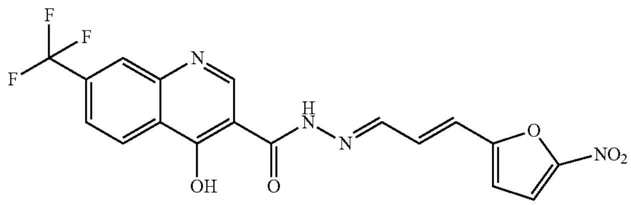 [SMILES: O=C(N/N=C/C=C/c1ccc([N+](=O)[O-])o1)c1cnc2cc(C(F)(F)F)ccc2c1O] | (E)-4-hydroxy-N'-((E)-3-(5-nitrofuran-2-yl)allylidene)-7-(trifluoromethyl)quinoline-3-carbohydrazide | 15.0 |
| CBU-040 | 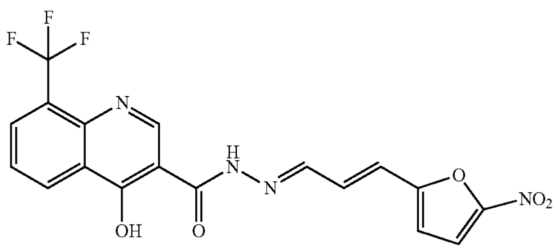 [SMILES: O=C(N/N=C/C=C/c1ccc([N+](=O)[O-])o1)c1cnc2c(C(F)(F)F)cccc2c1O] | (E)-4-hydroxy-N'((E)-3-(5-nitrofuran-2-yl)allylidene)-8-(trifluoromethyl)quinoline-3-carbohydrazide | 10.0 |
| CBU-041 | 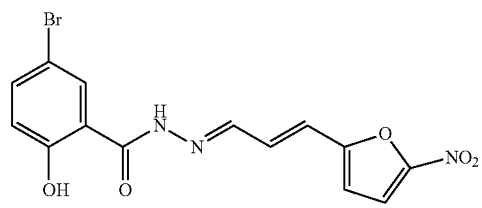 [SMILES: O=C(N/N=C/C=C/c1ccc([N+](=O)[O-])o1)c1cc(Br)ccc1O] | (E)-5-bromo-2-hydroxy-N'-((E)-3-(5-nitrofuran-2-yl)allylidene)benzohydrazide | 10.0 |
| CBU-042 | 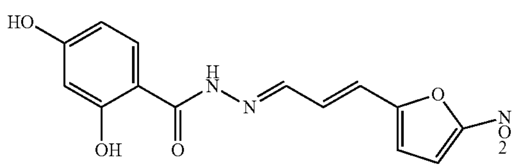 [SMILES: O=C(N/N=C/C=C/c1ccc([N+](=O)[O-])o1)c1ccc(O)cc1O] | (E)-2,4-dihydroxy-N'-((E)-3-(5-nitrofuran-2-yl)allylidene)benzohydrazide | 40.0 |
| CBU-043 | 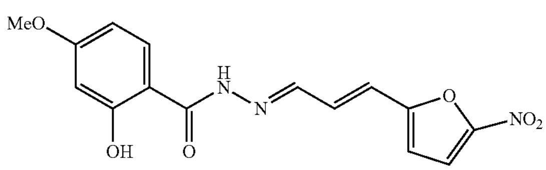 [SMILES: COc1ccc(C(=O)N/N=C/C=C/c2ccc([N+](=O)[O-])o2)c(O)c1] | (E)-2-hydroxy-4-methoxy-N'-((E)-3-(5-nitrofuran-2-yl)allylidene)benzohydrazide | 30.0 |
| CBU-045 | 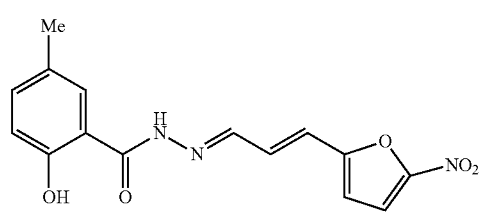 | (E)-2-hydroxy-5-methyl-N'-((E)-3-(5-nitrofuran-2-yl)allylidene)benzohydrazide | 6.0 |
| CBU-046 | 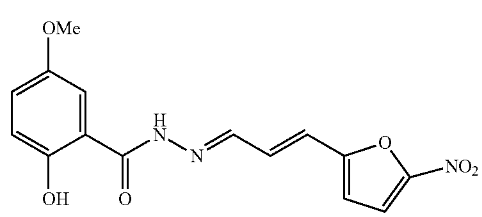 [SMILES: COc1ccc(O)c(C(=O)N/N=C/C=C/c2ccc([N+](=O)[O-])o2)c1] | (E)-2-hydroxy-5-methoxy-N'-((E)-3-(5-nitrofuran-2-yl)allylidene)benzohydrazide | 10.0 |

TABLE I-continued

| Compound | Structure | Name | IC50 |
|---|---|---|---|
| CBU-047 | 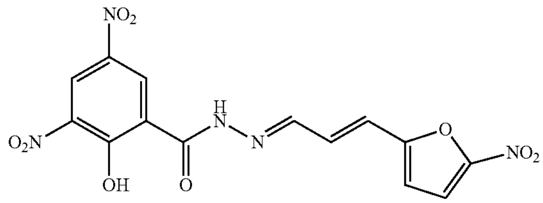 [SMILES: O=C(N/N=C/C=C/c1ccc([N+](=O)[O-])o1)c1cc([N+](=O)[O-])cc([N+](=O)[O-])c1O] | (E)-2-hydroxy-3,5-dinitro-N'-((E)-3-(5-nitrofuran-2-yl)allylidene)benzohydrazide | 30.0 |
| CBU-049 | 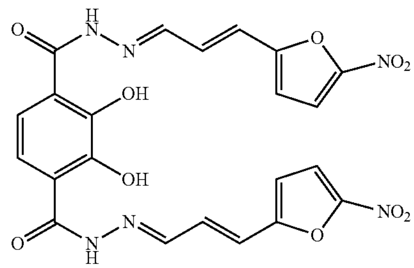 [SMILES: O=C(N/N=C/C=C/c1ccc([N+](=O)[O-])o1)c1ccc(C(=O)N/N=C/C=C/c2ccc([N+](=O)[O-])o2)c(O)c1O] | (N'1E,N'4E)-2,3-dihydroxy-N'1,N'4-bis((E)-3-(5-nitrofuran-2-yl)allylidene)terephthalohydrazide | 1.5 |
| CBU-051 | 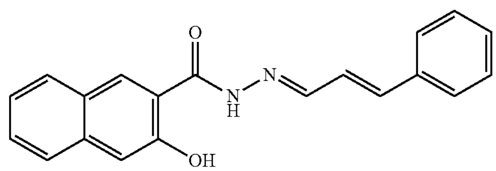 [SMILES: O=C(N/N=C/C=C/c1ccccc1)c1cc2ccccc2cc1O] | (E)-3-hydroxy-N'-((E)-3-phenylallylidene)-2-naphthohydrazide | 10.0 |
| CBU-054 | 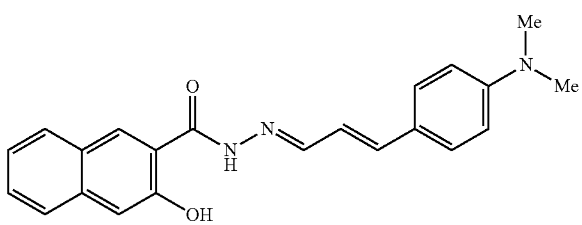 [SMILES: CN(C)c1ccc(/C=C/C=N/NC(=O)c2cc3ccccc3cc2O)cc1] | (E)-N'-((E)-3-(4-(dimethylamino)phenyl)allylidene)-3-hydroxy-2-naphthohydrazide | 15.0 |
| CBU-055 | 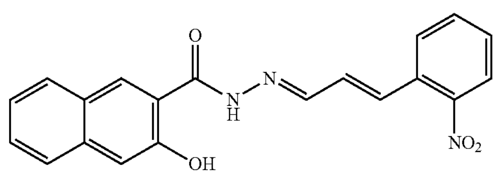 [SMILES: O=C(N/N=C/C=C/c1ccccc1[N+](=O)[O-])c1cc2ccccc2cc1O] | (E)-3-hydroxy-N'-((E)-3-(2-nitrophenyl)allylidene)-2-naphthohydrazide | 6.0 |
| CBU-061 | 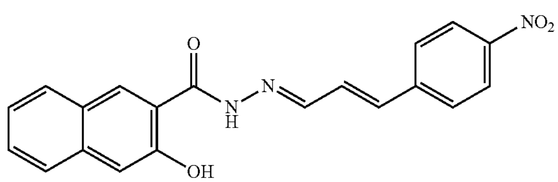 [SMILES: O=C(N/N=C/C=C/c1ccc([N+](=O)[O-])cc1)c1cc2ccccc2cc1O] | (E)-3-hydroxy-N'-((E)-3-(4-nitrophenyl)allylidene)-2-naphthohydrazide | 5.0 |
| CBU-062 | 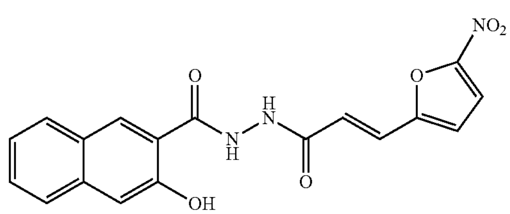 [SMILES: O=C(/C=C/c1ccc([N+](=O)[O-])o1)NNC(=O)c1cc2ccccc2cc1O] | (E)-3-hydroxy-N'-(3-(5-nitrofuran-2-yl)acryloyl)-2-naphthohydrazide | 2.5 |

TABLE I-continued

| Compound | Structure | Name | IC50 |
|---|---|---|---|
| CBU-073 | (structure) | | 3.0 |

Example 4

Structure Activity Relationship (SAR) Analysis of EERI

An analysis of structure-activity relationships (SAR) of EERI is performed. The structures of EERI and structurally related compounds are shown in panel (a) of FIG. 1.

Cytotoxicity of EERI and the structurally-related compounds is illustrated in the graph shown in panel (b) of FIG. 1. In the experiments summarized in the graph, a multiple myeloma and mantle cell lymphoma (MCL) cell line JEKO-1 is used to determine cell viability in vitro as a function of concentration of the compounds. JEKO-1 cells are kept in RPMI medium with 10% fetal calf serum (FCS). Cells grown to density $1 \times 10^6$/ml are seeded into 96 well plates at a concentration of $4 \times 10^5$/ml and incubated for 2 days at the indicated concentrations of a compound. The cells are grown to density $1 \times 10^6$/ml prior to testing. All compounds were initially dissolved in DMSO as 10 mM stock. Controls were untreated cells or cells treated with DMSO. Cell viability after each treatment is measured by a colorimetric assay using 3-(4,5-dimethylthiazol-2-yl)-2,5-diphenyltetrazolium bromide (MTT) (Chemicon, Temecula, Calif.), using the manufacturer's instructions. In the graph, the error bar on each data point indicates the standard deviation (SD) of three measurements. While the 5138380 compound shows little effect on cell viability, 5-nitrofuryl-acrolein shows cytotoxic activity at a concentration lower than that shown by EERI. Compound CBU-026, also shows cytotoxic activity but requires higher concentration than EERI.

EERI cytotoxicity, like that of bortezomib, requires up-regulation of the Bcl-2 homology 3(BH3)-only pro-apoptotic protein NOXA (also known as PMAIP1) Similar to bortezomib, EERI activates NOXA via a mechanism that requires cooperation between two processes. First, EERI elicits an integrated stress response at the ER to activate the CREB/ATF transcription factors activating transcription factor 3 (ATF3) and activating transcription factor 4 (ATF4) which form a complex that can bind and activate the NOXA promoter. Second, EERI also blocks ubiquitination of histone H2A to relieve its inhibition of NOXA transcription.

Expression of ATF3, ATF4, NOXA, and p97 in JEKO-1 cells after treatment with EERI or the structurally-related compounds is compared in the images shown in panel (c) of FIG. 1. Whole cell extracts from JEKO-1 cells exposed to the indicated compounds at either 2.5 μM for 5-nitrofuryl-acrolein or 10 μM for the others for 8 hrs are subjected to immunoblotting analyses using antibodies to ATF3, ATF4, NOXA, and p97, respectively.

Among the tested compounds shown, only treatment with 5-nitrofuryl-acrolein, EERI, or CBU-026 results in an expression level of ATF3, ATF4 and NOXA comparable to that present after treatment with EERI.

Figure 2:
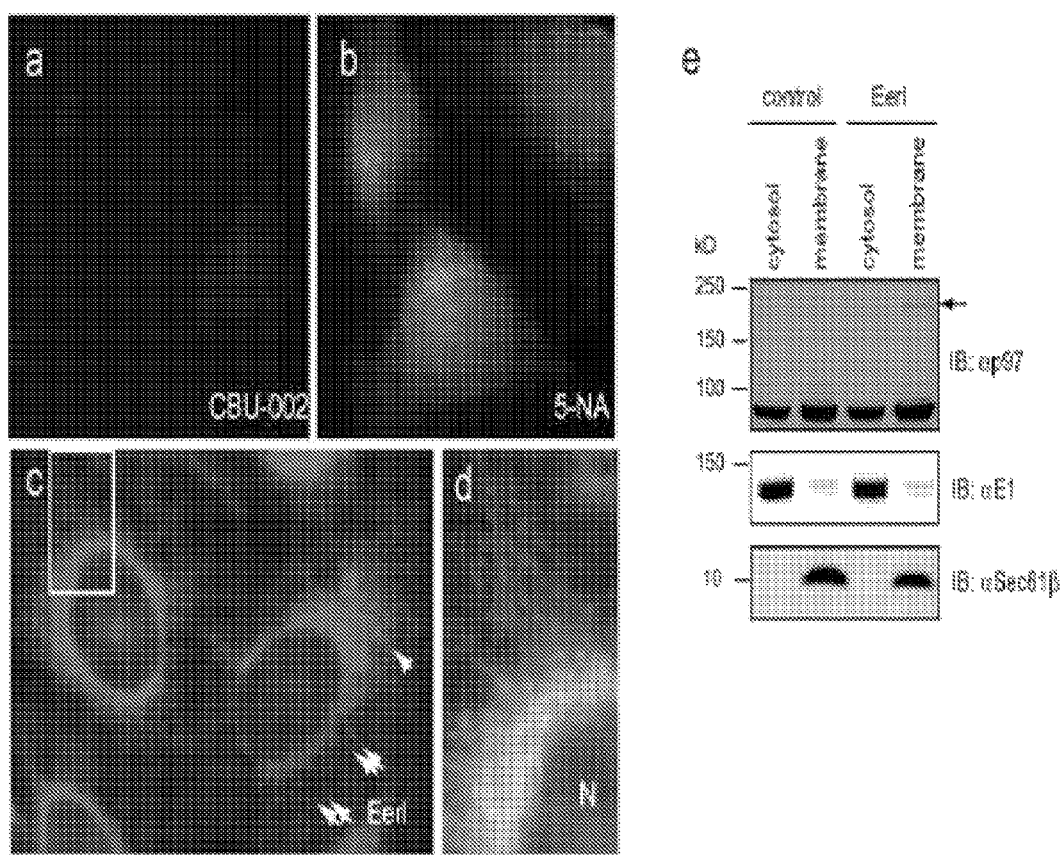
FIG. 2, panels a-d, shows images obtained by fluorescence microscopy of the localization of EERI, 5-nitrofuryl-acrolein (5-NA), or the compound CBU-002 in HeLa cells, with panel d showing an enlarged view of the boxed area in panel c with "N" denoting the nucleus. Panel e presents images of the immunoblot analysis with the indicated antibodies of proteins extracted from membrane or cytosol fractions of 293T cells grown in the presence or absence (control) of 10 μM EerI for 6 hr. Arrow indicates an oligomerized p97 species as a result from EerI treatment.

Subcellular localization of EERI, 5-nitrofuryl-acrolein (5-NA), and the compound 5138380 (CBU-002) is also compared. HeLa cells are treated with the indicated compounds at 10 μM for 1 h. Fluorescence images were obtained using a Zeiss Axiovert200 fluorescence microscope equipped with a 63× oil immersion Plan Apochromat objective and standard filter sets (FITC and rhodamine). Results are shown in FIG. 2. EERI-treated cells (panel c) display a strong fluorescence signal in a perinuclear reticulum-like pattern, indicative of ER localization. Arrows in panel c indicate some EerI-stained vesicles that may be derived from the ER or the endocytic system. Panel d shows an enlarged view of the boxed area in panel c that shows localization of EerI to a perinuclear reticulum-like membrane compartment in cells. In contrast, 5-nitrofuryl-acrolein-treated cells (panel b) show a uniform staining pattern with some punctae, suggesting that 5-NA is ubiquitously distributed in cells. The compound 5138380 (panel a) produces no fluorescence signal from the cells and was used as a negative control.

It was further demonstrated that EerI preferentially affects membrane associated p97 in experiments in which 293T cells were either untreated or treated with EerI at 10 μM for 6 hr. Cells were fractionated into membrane and cytosol fractions. Proteins extracted from these fractions were analyzed by immunoblotting with antibodies to p97, E1, and Sec61β, and ER-resident protein as shown in FIG. 2 e. A slow migrating p97 species, likely representing oligomerized p97 (indicated by the arrow) induced by EerI (discussed further below) is primarily in the membrane fraction, not in the cytosol fraction. These results suggest that EerI can associate with the ER membrane to interfere selectively with the function of membrane-associated p97.

Figure 11:
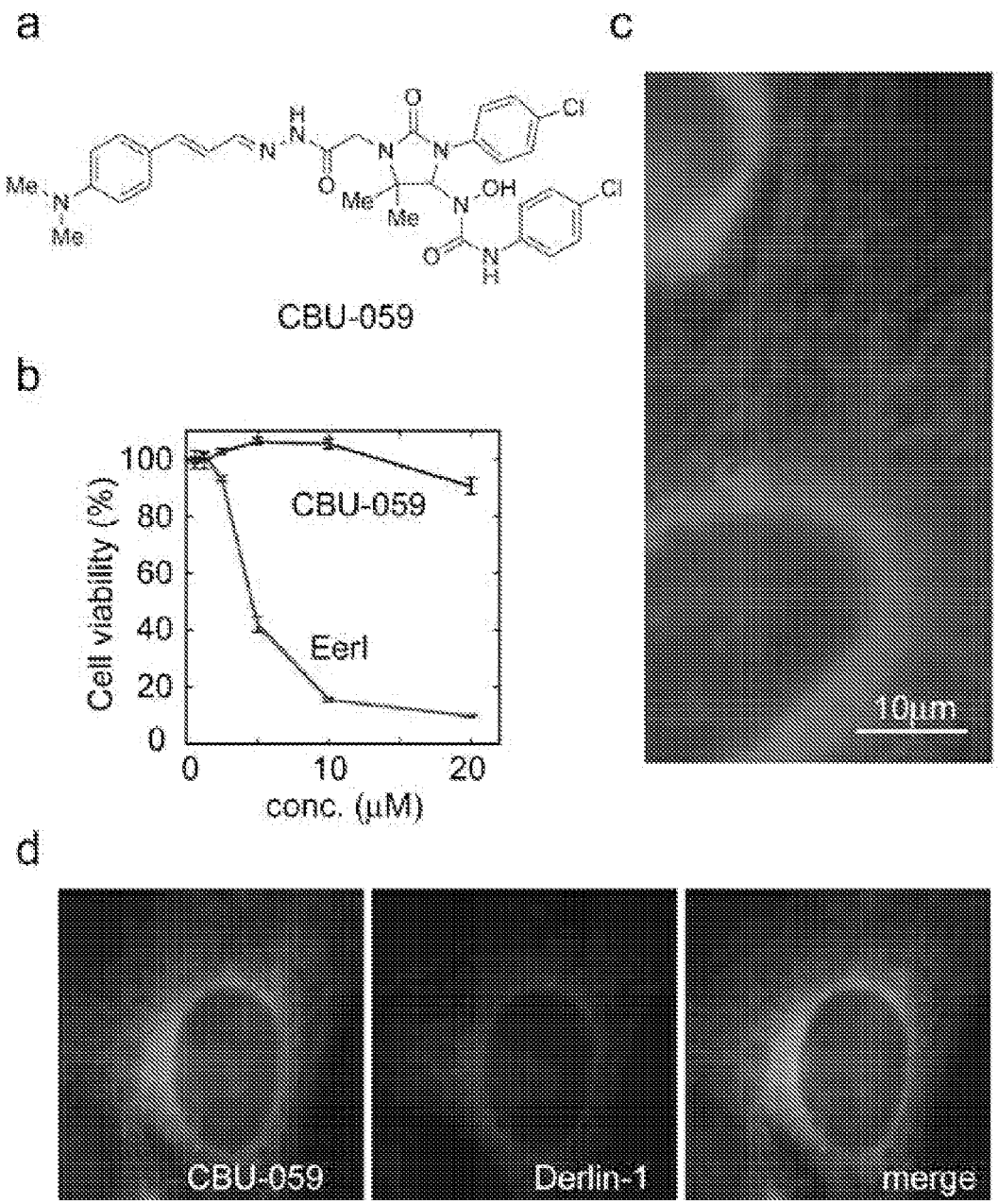
FIG. 11. a, The structure of CBU-059. b, a plot of percent cell viability as a function of CBU-059 or EerI concentration. c, fluorescent microscope image of CBU-059 (3 μM, 1 hour) staining a perinuclear reticulum-like membrane compartment of HeLa cells. d, fluorescent microscope images of CBU-059 or the ER membrane protein Derlin-1 in HeLa cells.

To further characterize the membrane association of the aromatic domain of EerI, the nitrofuran-containing (NFC) domain is replaced with several aldehydes that might give rise to a stronger fluorescence signal. The resulting compounds were predicted to be likely to be non-toxic as they did not contain the NFC moiety, but that they should be localized to the ER if the aromatic domain of EerI was capable of binding to the ER membrane. One of the resulting compounds CBU-059 (FIG. 11a) indeed produced a stronger fluorescence signal than EerI and had little effect on the viability of JEKO-1 cells (FIG. 11b). When exposed to CBU-059, cells displayed perinuclear ER-like staining pattern resembling EerI-treated cells (FIG. 11c). Double labeling experiments showed that CBU-059 co-localized with Derlin-1 (FIG. 11d), an ER resident protein. These results demonstrate that the aromatic domain in EerI is sufficient to recruit EerI to the ER membrane.

The strength of EerI binding to recombinant p97 purified from *E. coli* was tested using surface plasma resonance (SPR). Surface plasmon resonance interaction experiments were carried out at 25° C. on a Biacore T100 system (GE healthcare). Recombinant wild type or mutant p97 was covalently attached to a carboxymethyl dextran-coated gold surface (CM5 Chip; GE healthcare) using an amide couple kit following the manufacturer's suggested protocol. Briefly, the carboxymethyl group of dextran was activated with N-ethyl-N'-(3-dimethylaminopropyl)carbodiimide (EDC) and N-hydroxysuccinimide (NHS). Then, p97 in a 10 mM sodium acetate (pH 4.5) buffer was injected at a flow rate of 10 µl/min with 2 min contact time and immobilized at a level of ~8,000 RU. Any remaining reactive sites in the flow cell were blocked by ethanolamine. The drug association and dissociation were monitored at a flow rate of 20 mL/min with the analyte concentration ranging from 3.125 µM to 50 µM in a buffer containing 10 mM HEPES (pH 7.4), 150 mM NaCl, 0.005% v/v Surfactant P20. Regeneration of the chip was achieved by extended washing with the analyte buffer. SPR signal was normalized using a reference flow cell containing no p97. For each compound, three independent measurements were made. To calculate the affinity of EerI to p97, the data from each binding experiment were fit to a Michaelis-Menton model using KaleidaGraph software. The Rmax was then calculated, and the binding relative to the Rmax from three independent experiments was averaged. The averaged binding data were used to calculate the Kd.

Figure 8:
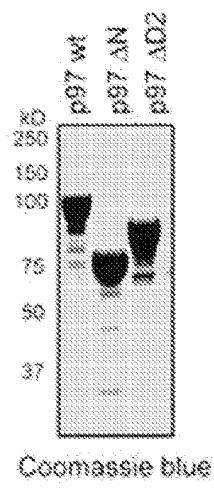
FIG. 8. a, Coomassie blue-stained gel of purified wild type and mutant p97 proteins used in the binding experiments. b, Surface plasmon resonance analyses of EerI interactions with p97 or a mutant p97 lacking its N-terminal domain (p97 ΔN) shown as a function of EERI concentration with the binding signal normalized relative to the calculated Rmax from three independent experiments. Error bar, SD (n=3). c, Images of silver-stained SDS-PAGE analysis of limited trypsin digestions as a function of time of p97 in the presence of EerI. Arrows indicate p97 fragments partially protected by EerI. The bracket indicates p97 degradation products. d, Whole cell extracts from cells treated with EerI for the indicated time periods were analyzed by immunoblotting with the indicated antibodies. The arrow indicates an oligomerized p97 species caused by EerI treatment.
Figure 8:
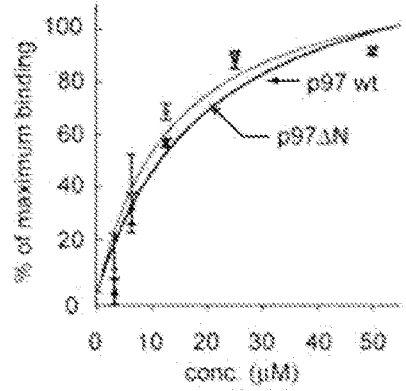
Figure 8:
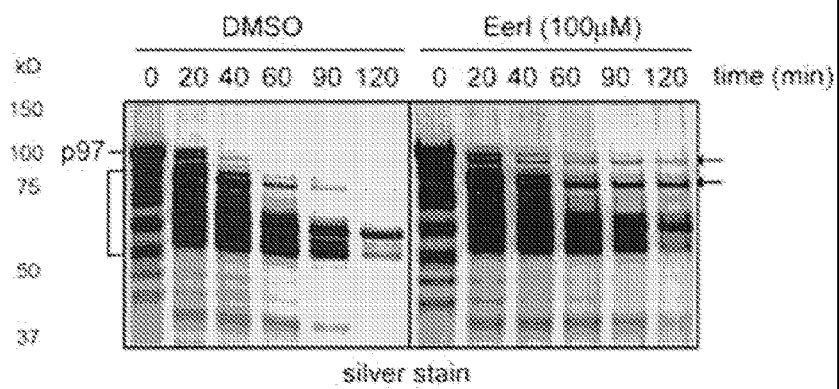
Figure 8:
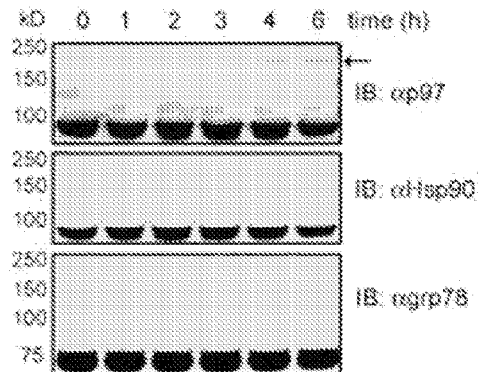

Analysis of the EERI concentration dependent response curves yielded an estimated $K_d$ of 5-10 µM (FIG. 8b). Binding of EerI with two p97 mutants that lacked either the N-terminal co-factor binding domain (p97ΔN) or the second ATPase domain (p97ΔD2) was tested to determine which domain in p97 was critical for EerI interaction. The results showed that EerI had similar affinity to the wild type and mutant p97 proteins (FIG. 8a, b, data not shown). From these results, it was concluded that EerI most likely binds p97 at a site in the D1 ATPase domain.

To understand how EerI binding might affect p97 function, in vitro ATPase activity of p97 in the presence of EerI was measured. No effect of EerI on the p97 ATPase activity was found (data not shown).

Sensitivity of p97 to limited trypsin digestion in the presence and absence of EerI was tested to determine whether binding of EerI to p97 could alter p97 conformation. The purified p97 protein (1.5 µg) was incubated at in a buffer containing 200 ng trypsin in 50 µl volume. Samples were taken out at different time points and mixed with the Laemmli buffer before SDS-PAGE and silver staining analyses. Preincubation of EerI with purified p97 caused a delay in the proteolysis of two p97 fragments by trypsin (FIG. 8c), suggesting that a conformational change occurs in p97 upon binding to EerI.

Further, a fraction of p97 in EerI-treated cells displayed reduced motility on SDS-PAGE gel. This effect was specific as no such high molecular weight species could be detected for several other ATPases in EerI-treated cells (FIG. 8d). Together, these results indicate that EerI alters p97 conformation to form non-functional p97 oligomers in cells (with a small fraction of such oligomers being resistant to SDS treatment).

Figure 9:
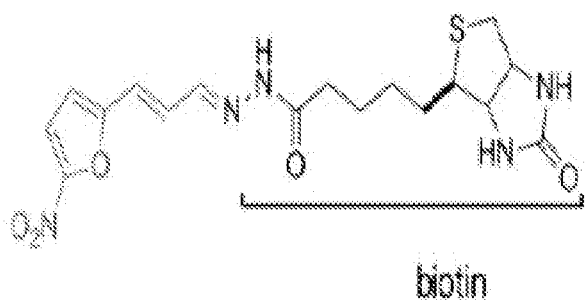
FIG. 9. a, The structure of biotinylated NFC (B-NFC or CBU-032). b, Images of immunoblots of precipitates of monomeric avidin beads immobilized with CBU-032 or biotin incubated with the indicated recombinant proteins. c, Images of immunoblots of precipitates of monomeric avidin beads immobilized with CBU-032 or biotin incubated with the indicated His-tagged proteins were tested.
Figure 9:
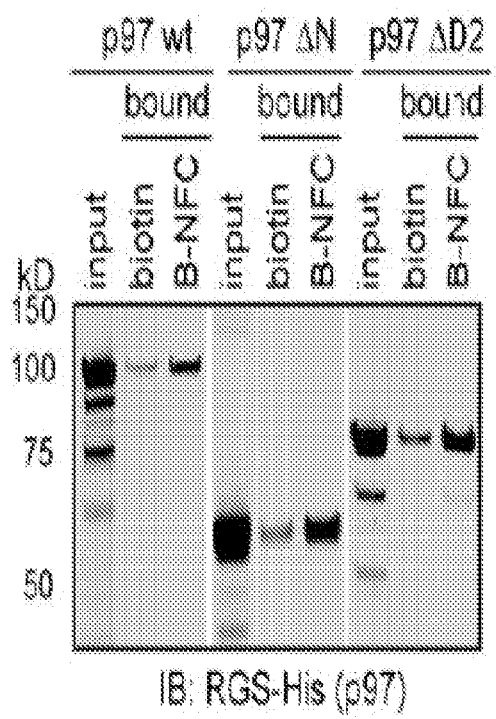
Figure 9:
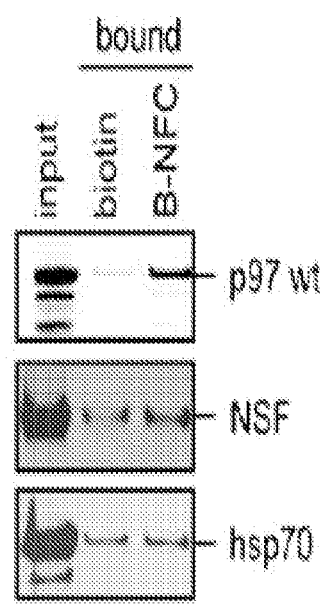

To test the hypothesis that EerI might bind p97 via the nitrofuran-containing (NFC) domain, a biotin moiety was conjugated to 5-nitrofuryl-acrolein (5-NA) to generate a biotinylated NFC domain (B-NFC) (FIG. 9a). B-NFC was immobilized on monomeric avidin beads by incubating 50 mM compound with the beads in a binding buffer containing 10 mM HEPES, pH 7.2, 150 mM sodium chloride, 0.005% Surfactant P20. The beads were then incubated with the 0.5 mM purified p97 proteins in 500 ml binding buffer at 4 degree for 1 h. The beads were washed for 3 times with the binding buffer and bound materials were eluted by incubating the beads with binding buffer comprising 4 mM biotin and analyzed by SDS-PAGE and immunoblotting. Beads with immobilized biotin were used as a negative control.

B-NFC consistently precipitated more p97, than biotin, (FIG. 9b). Consistent with the SPR studies on EerI, p97 mutants that lacked either the N-terminal domain (p97ΔN) or the D2 ATPase domain (p97ΔD2) also bound to 5-NA (FIG. 9b). This interaction was specific to p97 as neither the heat shock protein Hsp70, nor the homologous AAA ATPase, N-ethylmaleimide-sensitive factor (NSF), showed significant binding to B-NFC, (FIG. 9c). These results demonstrate that EerI can directly interact with p97 via the NFC domain.

To further confirm that both EerI and 5-NA can influence p97 function in cells, the gene expression pattern of EerI-treated cells is compared to that of 5-NA-treated cells using whole genome array hybridization. If two chemicals target the same gene, the change in gene expression profile in response to these compounds should overlap significantly and genes affected by these compounds should be similarly influenced when the target gene is inhibited by a siRNA-mediated knock down approach. These studies are performed in 293T cells because they are highly transfectable, making them well suited for genetic manipulation by siRNA. Cells were treated with EerI, CBU-028, or 5-NA each at 10 µM in duplicates for 10 h. Total RNA was extracted using TRIzol reagent (Invitrogen, Carlsbad, Calif.), and subsequently purified using an RNeasy MinElute Cleanup kit (QIAGEN, Valencia, Calif.). For array hybridization, RNA samples were processed and analyzed by The National Institute of Diabetes and Digestive and Kidney Diseases (NIDDK) Microarray Core Facility. The Affymetrix gene expression analysis array for the human HG-U133A_2_0 was used (Affymetrix). The microarray signals were analyzed using the Affymetrix RMA algorithm. Up- and down-regulated genes were selected based on P values of <0.05 and fold change >2.0 or <−2.0 as assessed by ANOVA with Partek Pro software (Partek). Genes that were upregulated by >1.5 were sometimes used in analysis as indicated in the figure legend. To determine specific pathways, gene pathway analysis were conducted using software from Genego, Inc., using the statistical significant ANOVA gene list (p<0.05, fold change >1.5) represented on the chip. Microarray data is MIAME compliant and that the raw data has been deposited in the Gene Expression Omnibus (GEO) database (accession no. GSE23849).

For quantitative RT-PCR, cDNA was synthesized using the SuperScript™ First-Strand kit (Invitrogen, Carlsbad, Calif.). Real-time PCR was performed in triplicate using the SYBR green PCR Master mixture. β-actin was used for normalization.

Figure 10:
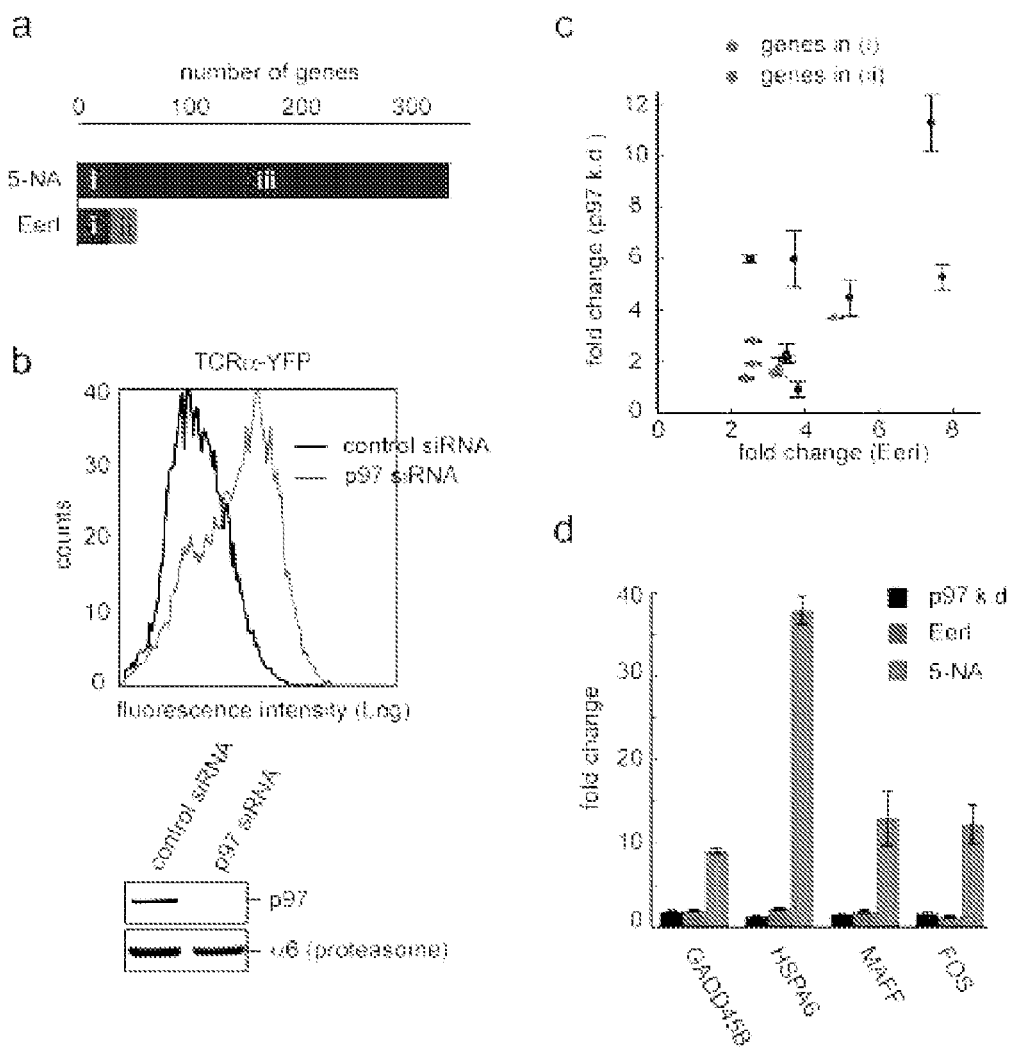
FIG. 10. a, a schematic plot of the number of genes whose expression was up- or down-regulated by at least 2-fold upon treatment with EerI (10 μM, 10 h) or 5-NA (10 μM, 10 h) in 293T cells: 29 genes were affected by both EerI and 5-NA (i), 25 genes were affected only by EerI (ii) and 306 genes were affected only by 5-NA (iii). b, Flow cytometry data showing degradation of TCRa-YFP in the presence p97 siRNA or control siRNA and an immunoblot with a p97 antibody of a fraction of the cells that were used to verify the knock-down efficiency. c, d, The effect of p97 depletion on the expression of EerI and 5-NA signature genes. c, The expression of selected genes in the categories i (8 genes, blue dots) and ii (7 genes, red dots) was determined by qRT-PCR using RNA prepared from p97 knock-down (k.d.) and control cells. The fold change upon p97 depletion was plotted against EerI-induced fold change. Error bars, SD (n=3) d, The expression of 4 genes in the category (iii) in p97 knock-down cells, or cells exposed to EerI (10 μM) or 5-NA (10 μM) was determined by qRT-PCR. Untreated cells were used to determine the basal expression of these genes, which was used to calculate the fold change.

5-NA treatment dramatically altered the gene expression landscape, resulting in changes in the expression of a large number of genes. The number of genes affected by EerI was significantly smaller (FIG. 10a). As expected, a large number of genes affected by EerI were similarly affected by 5-NA, defined as gene cohort (i). Pathway analyses showed that UPR-associated genes were enriched in this cohort. By contrast, genes only affected by EerI (cohort ii) or 5-NA (cohort iii) did not display the signature of UPR activation. Instead, they represented other pathways unrelated to ER homeostasis. These results suggest that 5-NA has a broader impact on cell physiology than EerI, suggesting that it may have additional targets other than p97. The conjugation of the aromatic module to 5-NA seems to restrict its action, making the ER a primary target of the resulting compound EerI.

To test whether the gene expression signature shared by 5-NA and EerI was indeed a result of p97 inhibition, p97 was knocked down in 293T cells. The knock-down efficiency was confirmed both by immunoblotting with an anti-p97 antibody and by monitoring the stabilization of the model ERAD substrate TCRα in p97 depleted cells (FIG. 10b). The effect of p97 depletion on the expression of representative genes upregulated by EerI and 5-NA was analyzed for 8 genes in cohort (i), 7 genes in cohort (ii), and 4 genes in cohort (iii). qRT-PCR analyses showed that all genes except for one in cohort (i) were significantly induced upon p97 depletion (>twofold). In contrast, only 2 out of the 7 genes in cohort (ii) were significantly upregulated in p97 knock-down cells (FIG. 10c), and none of the genes tested in cohort (iii) were induced by knock-down of p97 (FIG. 10d). These results confirm that p97 is a target of both EerI and 5-NA. Because the expression of more than 50% of EerI signature genes (cohort i) are similarly affected by p97 depletion, p97 appears to be a major target of EerI. By contrast, the majority of the 5-NA-affected genes (cohort iii) do not seem to result from p97 inhibition. Thus, 5-NA must have additional targets other than p97 in cells.

Example 5

In Vitro Assay to Determine Cytotoxic Activity Against Hematolgical Cancer Cells A selection of compounds are tested to determine their cytotoxic activity against JEKO-1 cells as described above in Example 4.

For each compound, the dose-percent cell viability curve is fit to obtain a half maximal inhibitory concentration (IC 50) using a four parameter logistic model. The cytotoxicity of each compound, reported as IC 50, is shown in the table below.

Example 6

Characterization of CBU-028

Compound CBU-028 (FIG. 3, panel a) was selected for further characterization with respect to its functional activities.

Figure 3:
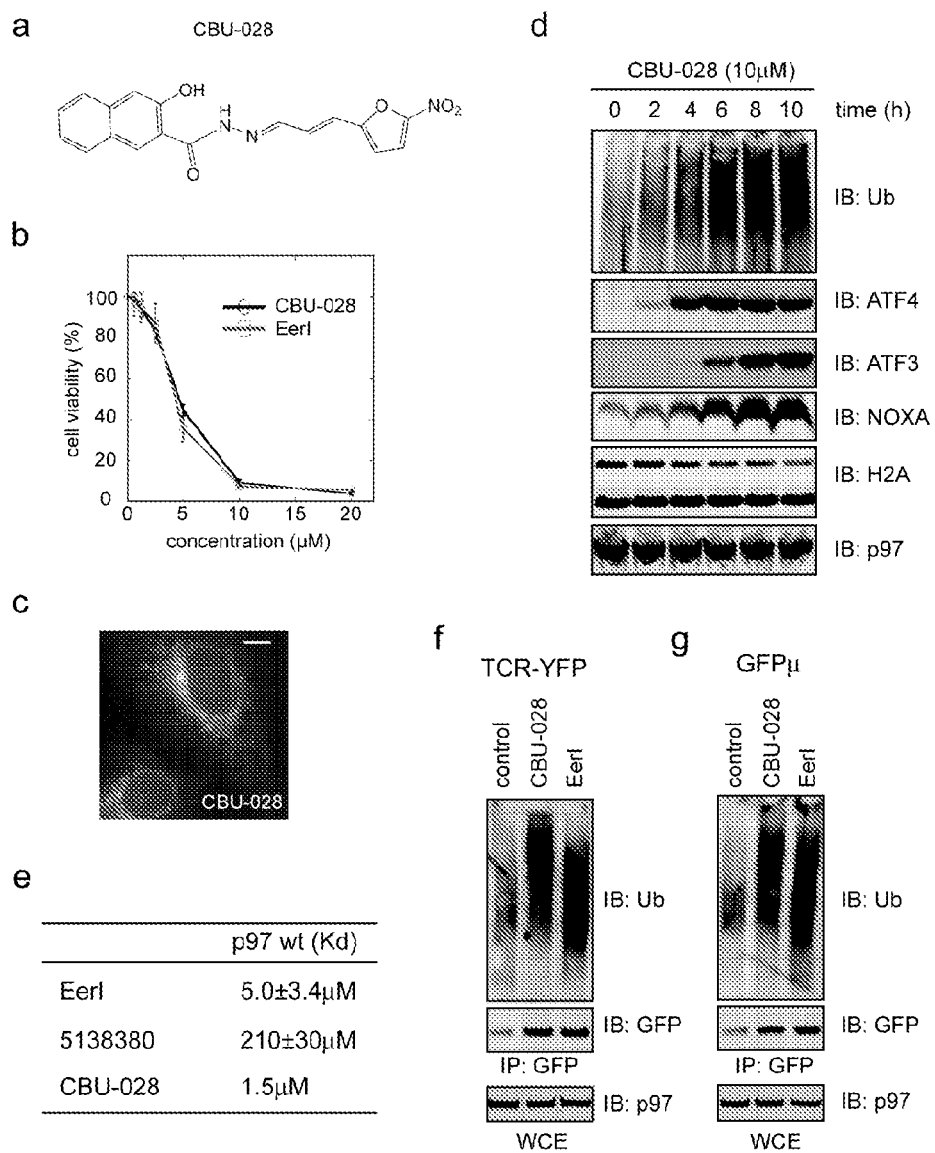
FIG. 3 shows the structure of compound CBU-028 (panel a), a graph of the percent cell viability as a function of concentration of compound CBU-028 compared to EERI (panel b); cellular localization of CBU-028 (panel c), effects on expression of ATF4, ATF3, NOXA, and on levels of ubiquitinated histone H2A in JEKO-1 cells as a function of time of treatment with 10 μM CBU-028 (panel d); dissociation constants (Kd) of EERI, compound 5138380, or CBU-028 binding to purified recombinant wild-type (wt) p97 protein panel e), a comparison of stabilization of the ERAD substrate TCRα-YFP in polyubiquitinated forms by 10 μM CBU-028 or EERI (panel f), and a comparison of stabilization of the soluble p97 substrate GFPμ in polyubiquitinated forms by 10 μM CBU-028 or EERI. (panel g)

The graph of percent cell viability as a function of concentration presented in FIG. 3, panel b, shows that cytotoxicity of CBU-028 with respect to JEKO-1 cells is similar to that for EERI. In these experiments, JEKO-1 cells, grown as described above, were treated with the indicated compounds for 48 h. Cell viability was measured by the MTT assay. The error bar on each data point represents the standard deviation for three replicate experiments.

The cellular localization in COS7 cells of CBU-028 is similar to that of EERI (See FIG. 2, panel c). COS7 cells are treated with 10 mM CBU-028 for 4 h and imaged using a fluorescence microscope. Results are shown in FIG. 3, panel c.

CBU-028 has other biological activities similar to those of EERI.

Expression of select genes in JEKO-1 cells treated with CBU-028 is determined. In the experiment shown in FIG. 3, panel d, JEKO-1 cells are treated with 10 μM CBU-028 for the indicated times. Whole cell extracts are obtained and analyzed by SDS-PAGE and immunoblotting with antibodies against the proteins ubiquitin (Ub), ATF4, ATF3, NOXA, histone H2A, and p97. Similar to EERI, CBU-028 induces expression of the ER stress markers ATF3 and ATF4, upregulates NOXA protein level, causes accumulation of polyubiquitinated proteins, and downregulates ubiquitinated histone H2A (upper band in H2A immunoblot).

The affinity of CBU-028, EERI, and compound 5138380 to purified p97 is measured by surface plasmon resonance (SPR). Wild type recombinant p97 (p97 wt) is purified from *E. coli* and covalently attached to a carboxymethyl dextran-coated gold surface (CM5 Chip; GE healthcare) using an amide coupling kit following a manufacture suggested protocol. Briefly, the carboxymethyl groups of the dextran are activated with N-ethyl-N'-(3-dimethylaminopropyl) carbodi-imide (EDC) and N-hydroxysuccinimide (NHS). The protein p9'7, at a concentration of 1.0 μM in a buffer containing 10 mM sodium acetate (pH 4.5), is immobilized at a level of ~8,000RU. Any remaining reactive sites in the flow cell are blocked by ethanolamine. Purified ubiquitin is also immobilized in a flow cell on the same chip to serve as a negative control. Association and dissociation of the compounds are monitored at a flow rate of 20 μL/min at concentrations ranging from 1.6 μM to 100 μM. The compounds are prepared in a buffer containing 10 mM HEPES (pH 7.4), 150 mM NaCl, 0.005% v/v surfactant P20. Regeneration of the chip is achieved by injecting a buffer containing 2M NaCl. The SPR signal is normalized using a reference flow cell containing no p97. Dissociation constants are obtained by analysis of the SPR signals and shown in FIG. 3, panel e.

Comparison of the effect of 10 μM CBU-028 or EERI on the ERAD substrate TCRα-YFP is shown in FIG. 3, panel f. 293T cells stably expressing TCRα-YFP are treated with the indicated compounds (10 mM) or as a control with DMSO for 10 h. Cells are lysed in RIPA buffer (50 mM Tris, pH 7.5, 1% NP40, 0.1% SDS, 0.5% sodium deoxycholate, 150 mM sodium chloride, 2 mM EDTA and a protease inhibitor cocktail). TCRα-YFP is immunoprecipitated from the cell extract using an anti-green fluorescent protein (GFP) antibody. The precipitated material is analyzed by SDS-PAGE and immunoblotting with antibodies against uUb and GFP. The whole cell extracts are also analyzed by SDS-PAGE and immunoblotting with antibodies against p. 97. CBU-028 and EERI both stabilize the ERAD substrate TCRα-YFP in polyubiquitinated forms.

Comparison of the effect of 10 μM CBU-028 or EERI on the soluble p97 substrate GFPμ is shown in FIG. 3, panel g. The experiments are performed as described above for TCRα-YFP, except that 293 T cells stably expressing GFP are used. CBU-028 and EERI both stabilize the soluble p97 substrate GFPμ in polyubiquitinated forms.

Example 7

Effect of NOXA on Cytotoxicity of CBU-028, EERI, or Bortezomib

Figure 4:
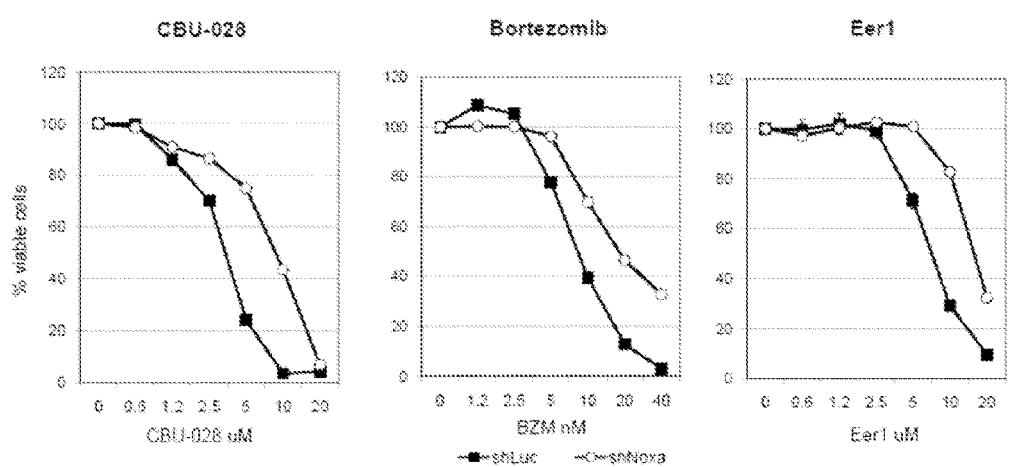
FIG. 4. Noxa is equally required for CBU-028 cytotoxicity as it is for bortezomib and EERI.

The effect of NOXA on cytotoxicity of CBU-028, EERI, or bortezomib is determined. FIG. 4 presents graphs comparing CBU-028, EERI, and bortezomib with respect to percent cell viability as a function of concentration, measured using JEKO-1 cells stably transfected with shRNAs to luciferase (shLuc, control, ■) or NOXA (shNoxa, ○, sequence: GATC-CCGGTGCACGTTTCATCAATTTGTTCAA-GAGACAAATTGATGAAACGTGCA CCTTTTT) after treatment with the compound for 24 hrs, with viability determined with MTT as described above and normalized to the untreated control.

The experiments show that blocking expression of NOXA with NOXA shRNA results in increasing the concentration of each compound required to achieve cytotoxicity.

Example 8

Cytotoxic Activity of CBU-028 or EERI Against Primary Cells

The cytotoxic activity of CBU-028 or EERI against primary cells is determined as a function of concentration. Cell viability of primary chronic lymphocytic leukemia (CLL) cells or normal peripheral blood mononuclear cells (PBMC) at a concentration of 5×10e6 cells/ml is determined after treatment with CBU-028 or EERI for 48 hrs in triplicates. Viability is determined using the MTT assay, as described previously, with data normalized to the untreated control.

Figure 5:
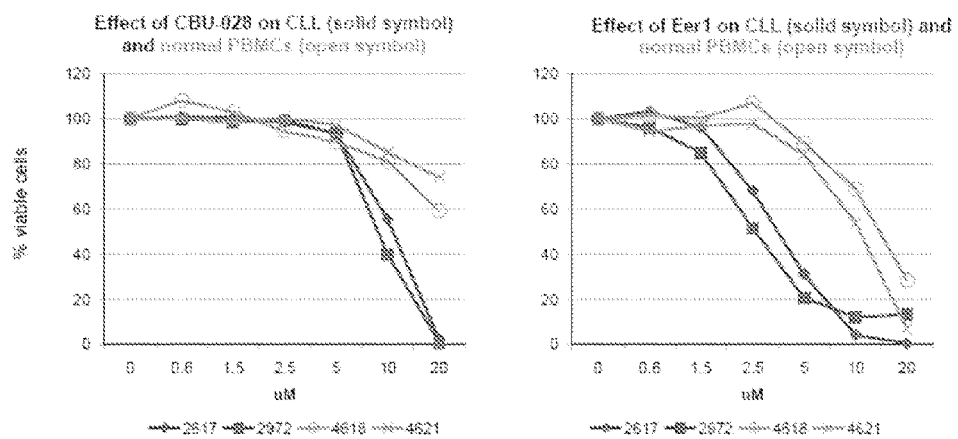
FIG. 5 presents graphs comparing CBU-028 and EERI with respect to percent cell viability as a function of concentration, measured using primary CLL cells and normal PBMC cells after treatment with the compound for 24 hours.
Figure 6:
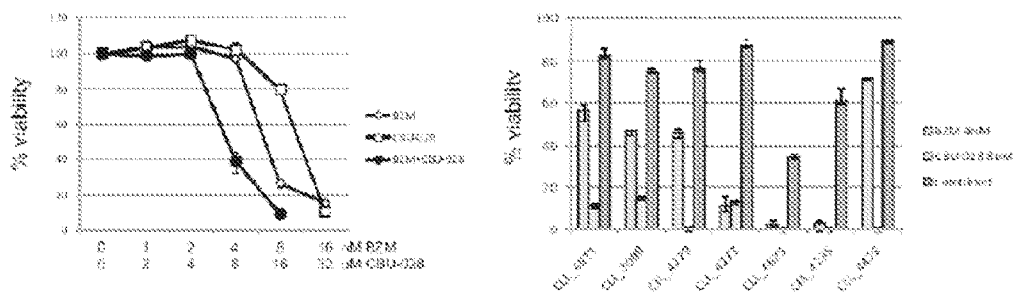
FIG. 6. CBU-028 Synergizes with Bortezomib Against CLL Cells. To test for synergy between BZM and CBU-028, CLL cells were incubated in-vitro to increasing concentrations of each compound individually as well as to a combination of both drugs. The combination was tested at a fixed molar relation of 1:2000, e.g. 4 nM BZM was combined with 8 uM CBU-028. $5 \times 10^6$ cells/mL were incubated for 48 hours and cell viability was measured with MTT. Synergy is found where the effect of the combination of the two compounds exceeds the additive effect of each compound separately. The left graph shown the result of a representative experiment (CLL_4235) across all concentrations tested. The graph on the right summarizes the data for 7 individual CLL patients.
Figure 7:
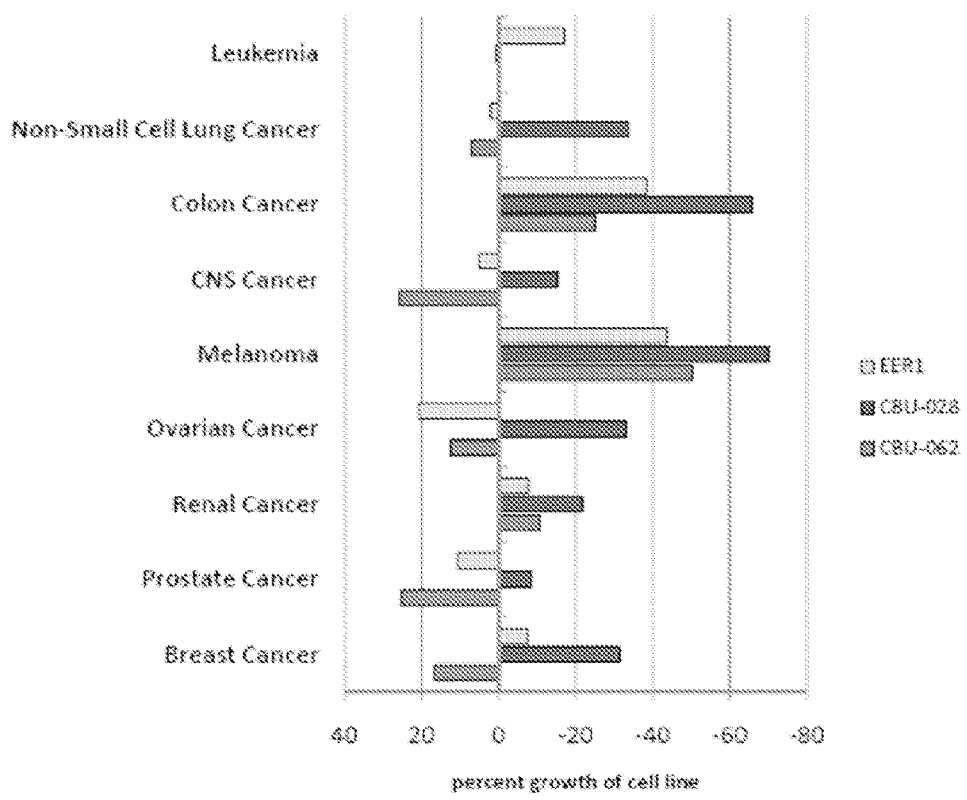
FIG. 7. Efficacy of ERAD inhibitors in the NCI 60 screen.

Results are shown in FIG. 5. PBMC are less sensitive to both EERI and CBU-028 than are the CLL cells. Additional cytotoxicity data for CBU-0028, CBU-0062 and EERI is given in TABLES II-IV.

TABLE II

CBU-028 CYTOTOXICITY.

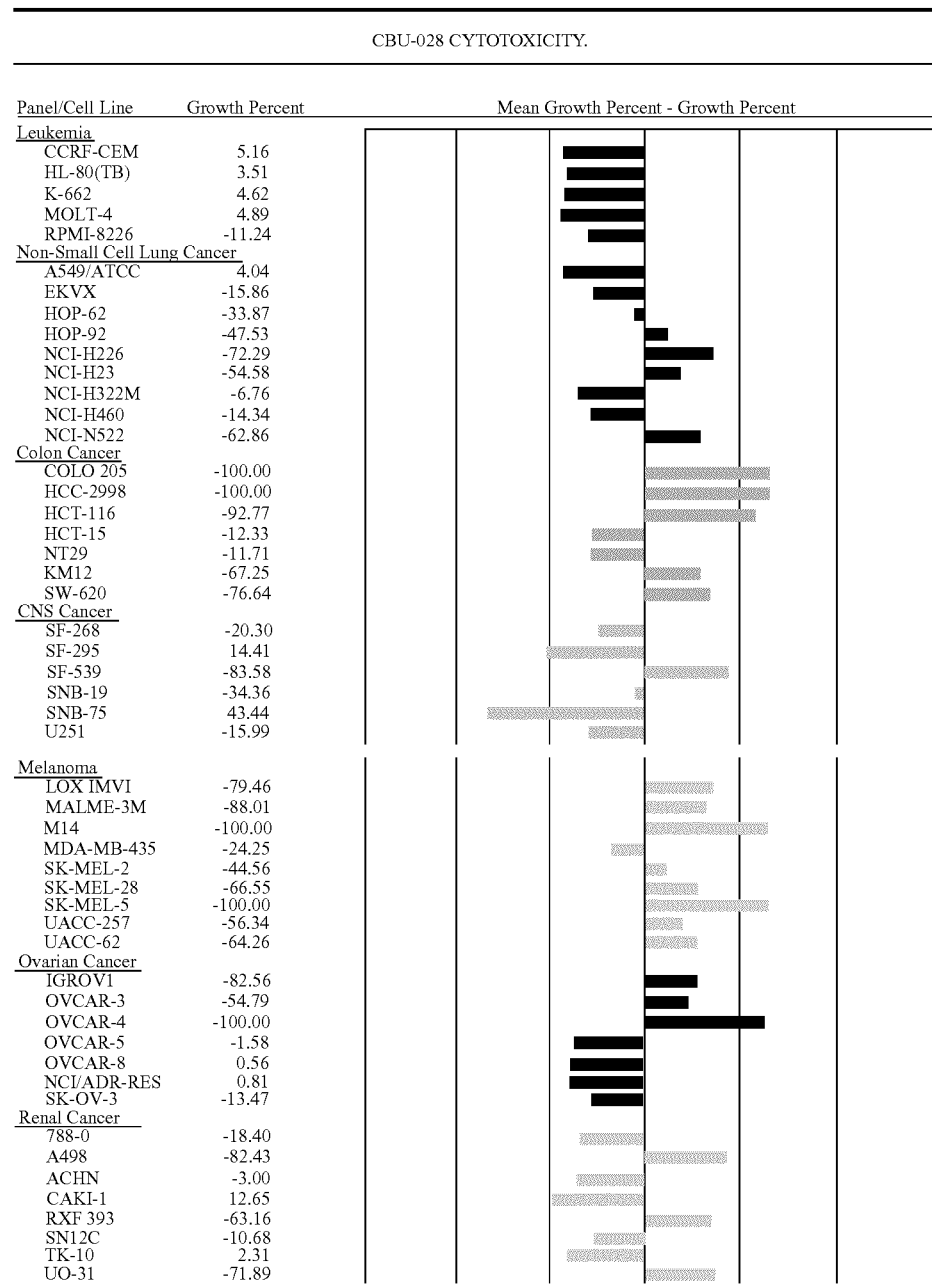

| Panel/Cell Line | Growth Percent |
|---|---|
| Leukemia | |
| CCRF-CEM | 5.16 |
| HL-80(TB) | 3.51 |
| K-662 | 4.62 |
| MOLT-4 | 4.89 |
| RPMI-8226 | -11.24 |
| Non-Small Cell Lung Cancer | |
| A549/ATCC | 4.04 |
| EKVX | -15.86 |
| HOP-62 | -33.87 |
| HOP-92 | -47.53 |
| NCI-H226 | -72.29 |
| NCI-H23 | -54.58 |
| NCI-H322M | -6.76 |
| NCI-H460 | -14.34 |
| NCI-N522 | -62.86 |
| Colon Cancer | |
| COLO 205 | -100.00 |
| HCC-2998 | -100.00 |
| HCT-116 | -92.77 |
| HCT-15 | -12.33 |
| NT29 | -11.71 |
| KM12 | -67.25 |
| SW-620 | -76.64 |
| CNS Cancer | |
| SF-268 | -20.30 |
| SF-295 | 14.41 |
| SF-539 | -83.58 |
| SNB-19 | -34.36 |
| SNB-75 | 43.44 |
| U251 | -15.99 |
| Melanoma | |
| LOX IMVI | -79.46 |
| MALME-3M | -88.01 |
| M14 | -100.00 |
| MDA-MB-435 | -24.25 |
| SK-MEL-2 | -44.56 |
| SK-MEL-28 | -66.55 |
| SK-MEL-5 | -100.00 |
| UACC-257 | -56.34 |
| UACC-62 | -64.26 |
| Ovarian Cancer | |
| IGROV1 | -82.56 |
| OVCAR-3 | -54.79 |
| OVCAR-4 | -100.00 |
| OVCAR-5 | -1.58 |
| OVCAR-8 | 0.56 |
| NCI/ADR-RES | 0.81 |
| SK-OV-3 | -13.47 |
| Renal Cancer | |
| 788-0 | -18.40 |
| A498 | -82.43 |
| ACHN | -3.00 |
| CAKI-1 | 12.65 |
| RXF 393 | -63.16 |
| SN12C | -10.68 |
| TK-10 | 2.31 |
| UO-31 | -71.89 |

TABLE II-continued

| | | |
|---|---|---|
| Prostate Cancer | | |
| PC-3 | 4.52 | |
| DU-146 | -21.66 | |
| Breast Cancer | | |
| MCF7 | -61.36 | |
| MDA-MB-231/ATCC | -15.93 | |
| HS 578T | 4.48 | |
| BT-549 | -9.91 | |
| T-47D | -65.49 | |
| MDA-MB-468 | -64.99 | |
| Mean | -36.64 | |
| Delta | 83.36 | |
| Range | 143.44 | |

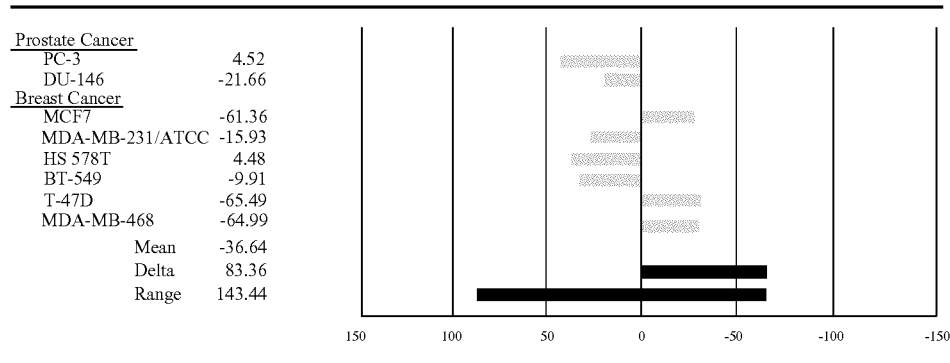

TABLE III

CBU-062 CYTOTOXICITY

| Panel/Cell Line | Growth Percent |
|---|---|
| Leukemia | |
| CCRF-CEM | 6.58 |
| HL-60(TB) | 1.21 |
| K-562 | 3.48 |
| MOLT-4 | 3.05 |
| RPMI-8226 | -6.98 |
| Non-Small Cell Lung Cancer | |
| A549/ATCC | 32.41 |
| EKVX | 38.60 |
| HOP-62 | 27.47 |
| HOP-92 | 4.15 |
| NCI-H226 | 0.68 |
| NCI-H23 | 6.76 |
| NCI-H322M | 23.26 |
| NCI-H460 | 9.04 |
| NCI-N522 | -79.47 |
| Colon Cancer | |
| COLO 205 | -7.38 |
| HCC-2998 | -18.41 |
| HCT-116 | -100.00 |
| HCT-15 | -62.67 |
| NT29 | 7.40 |
| KM12 | 11.63 |
| SW-620 | -5.85 |
| CNS Cancer | |
| SF-268 | -3.99 |
| SF-295 | 54.85 |
| SF-539 | 22.64 |
| SNB-19 | 33.47 |
| SNB-75 | 45.67 |
| U251 | 17.49 |
| Melanoma | |
| LOX IMVI | -10.47 |
| MALME-3M | -36.27 |
| M14 | -93.32 |
| MDA-MB-435 | -13.30 |
| SK-MEL-2 | -60.86 |
| SK-MEL-28 | -46.06 |
| SK-MEL-5 | -86.88 |
| UACC-257 | -16.49 |
| UACC-62 | -99.07 |
| Ovarian Cancer | |
| IGROV1 | -1.53 |
| OVCAR-3 | -37.34 |
| OVCAR-4 | 29.33 |
| OVCAR-5 | 45.70 |
| OVCAR-8 | 8.19 |
| NCI/ADR-RES | 5.33 |
| SK-OV-3 | 32.78 |
| Renal Cancer | |
| 786-0 | -23.77 |
| A498 | -51.02 |
| ACHN | -81.97 |
| CAKI-1 | 22.47 |
| RXF 393 | -20.81 |
| SN12C | 7.50 |
| TK-10 | 19.28 |
| UO-31 | 2.06 |

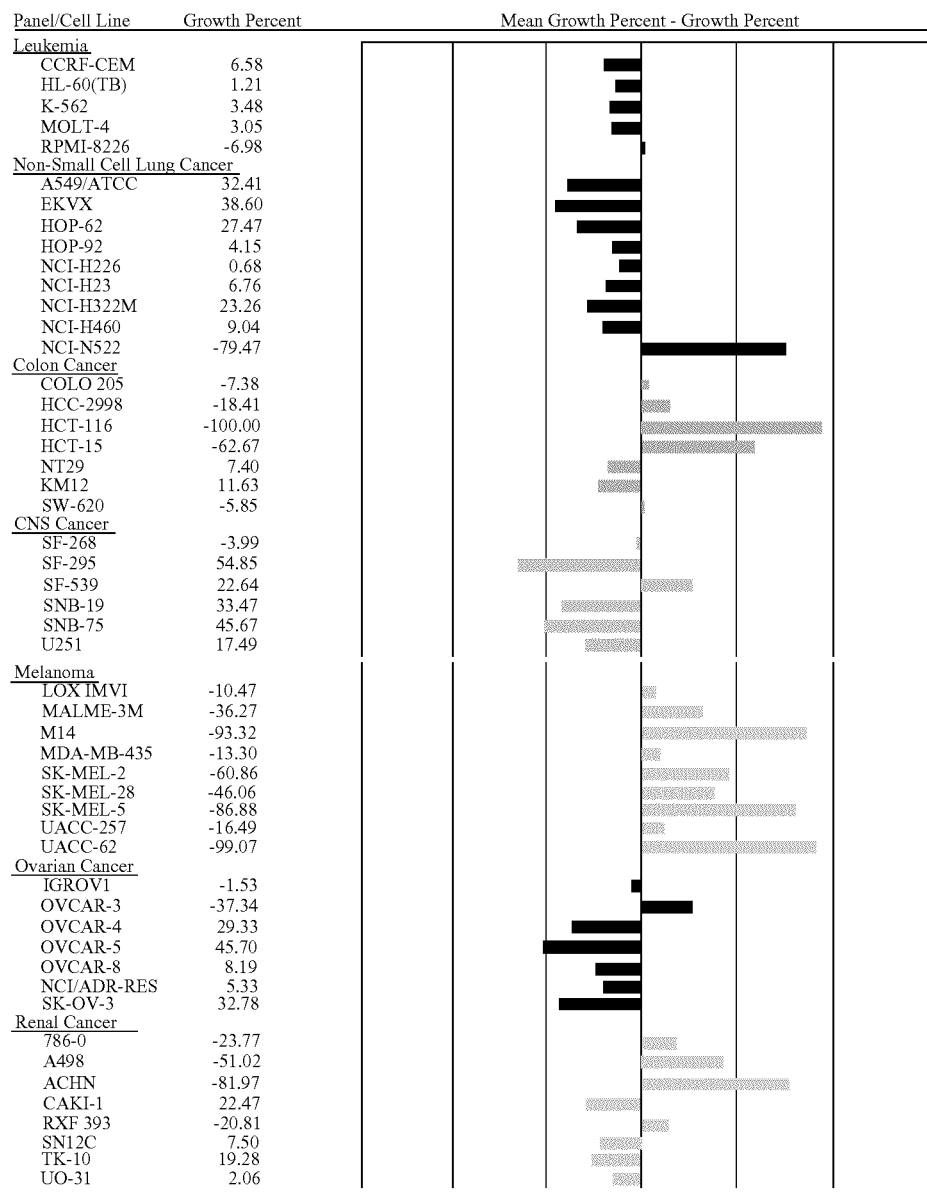

TABLE III-continued

| Panel/Cell Line | Growth Percent | |
|---|---|---|
| Prostate Cancer | | |
| PC-3 | 38.42 | |
| DU-146 | 11.72 | |
| Breast Cancer | | |
| MCF7 | 32.86 | |
| MDA-MB-231/ATCC | 21.01 | |
| HS 578T | 32.98 | |
| BT-549 | -1.88 | |
| T-47D | 2.44 | |
| MDA-MB-468 | 6.09 | |
| | Mean | -5.61 |
| | Delta | 94.39 |
| | Range | 154.85 |

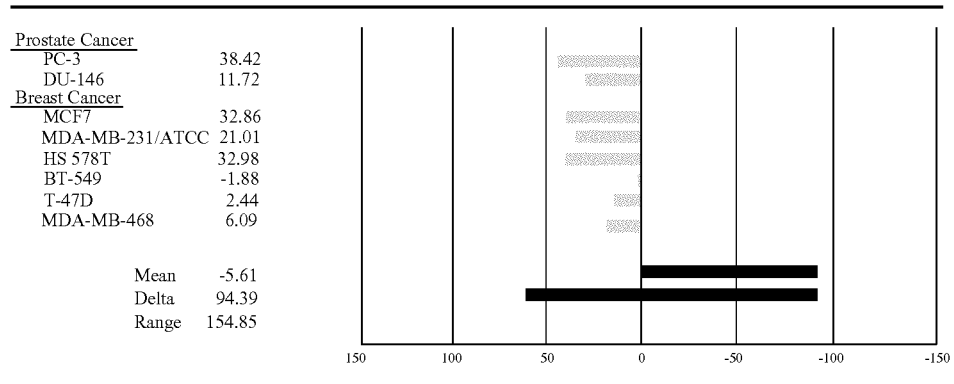

TABLE IV

| Panel/Cell Line | Growth Percent |
|---|---|
| Leukemia | |
| HL-60(TB) | -35.96 |
| K-562 | 13.15 |
| MOLT-4 | 21.53 |
| RPMI-8226 | -23.67 |
| SR | -13.14 |
| Non-Small Cell Lung Cancer | |
| A549/ATCC | 6.98 |
| EKVX | 29.78 |
| HOP-62 | 36.77 |
| HOP-92 | -30.92 |
| NCI-H226 | 25.84 |
| NCI-H23 | 3.01 |
| NCI-H322M | 48.98 |
| NCI-H460 | -13.13 |
| NCI-H522 | -88.45 |
| Colon Cancer | |
| COLO 205 | -81.26 |
| HCC-2998 | 90.57 |
| HCT-116 | -98.13 |
| HCT-15 | 37.47 |
| NT29 | -43.01 |
| KM12 | 23.10 |
| SW-620 | -15.72 |
| CNS Cancer | |
| SF-295 | 54.92 |
| SF-539 | -73.32 |
| SNB-19 | 48.61 |
| SNB-75 | 9.93 |
| U251 | -14.40 |
| Melanoma | |
| LOX IMVI | 0.58 |
| MALME-3M | -42.65 |
| M14 | 65.59 |
| MDA-MB-435 | -15.32 |
| SK-MEL-28 | 55.48 |
| SK-MEL-5 | -96.50 |
| UACC-257 | -33.68 |
| UACC-62 | -40.49 |
| Ovarian Cancer | |
| IGROV1 | -5.58 |
| OVCAR-3 | -26.76 |
| OVCAR-4 | 14.90 |
| OVCAR-5 | 6.40 |
| OVCAR-8 | 3.32 |
| NCI/ADR-RES | 94.99 |
| SK-OV-3 | 57.83 |
| Renal Cancer | |
| 786-0 | -46.95 |
| ACHN | 9.18 |
| CAKI-1 | 68.01 |
| RXF 393 | -77.92 |
| SN12C | -21.39 |
| TK-10 | 4.58 |
| UO-31 | 12.84 |

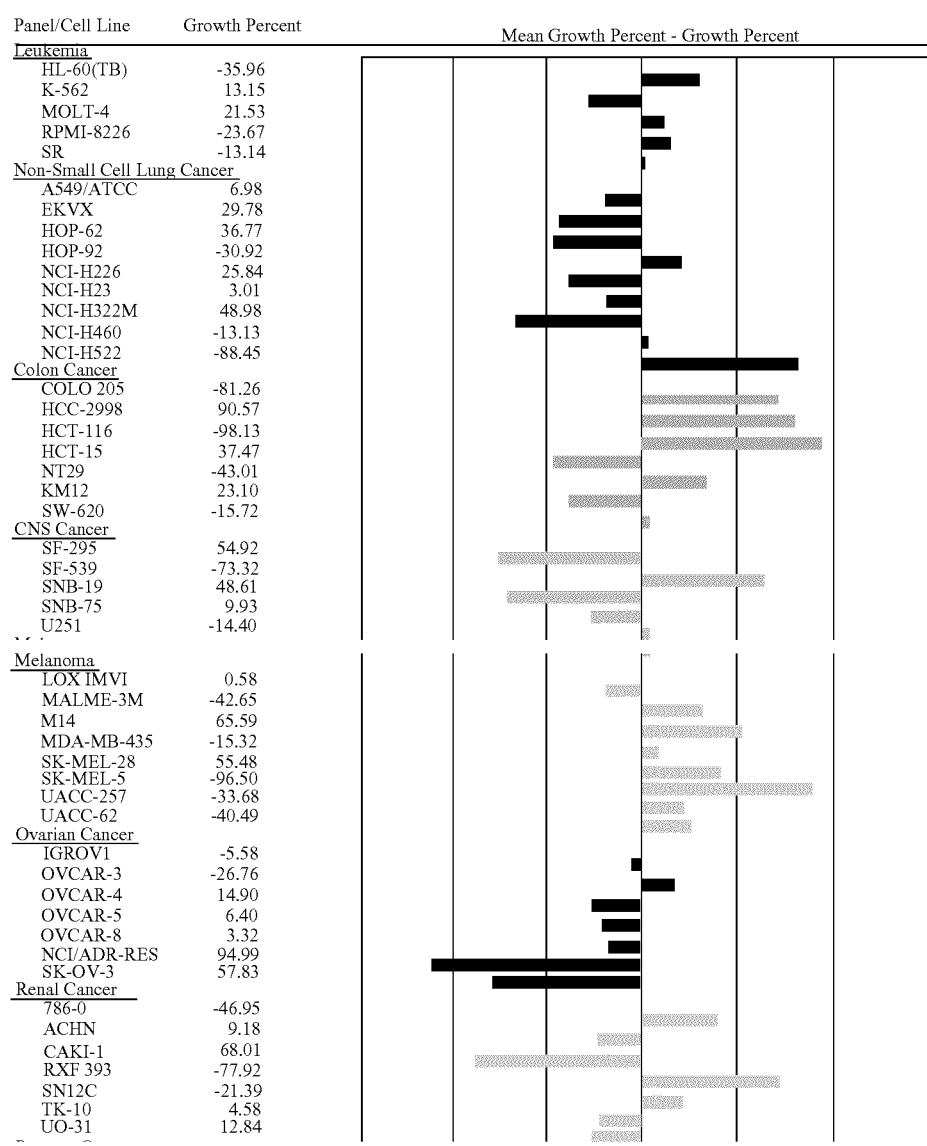

TABLE IV-continued

| Prostate Cancer | |
|---|---|
| PC-3 | 8.77 |
| DU-146 | 12.48 |
| Breast Cancer | |
| MCF7 | 7.37 |
| MDA-MB-231/ATCC | -48.75 |
| HS 578T | -11.41 |
| BT-549 | 19.14 |
| T-47D | 34.27 |
| Mean | -10.52 |
| Delta | 87.61 |
| Range | -193.12 |

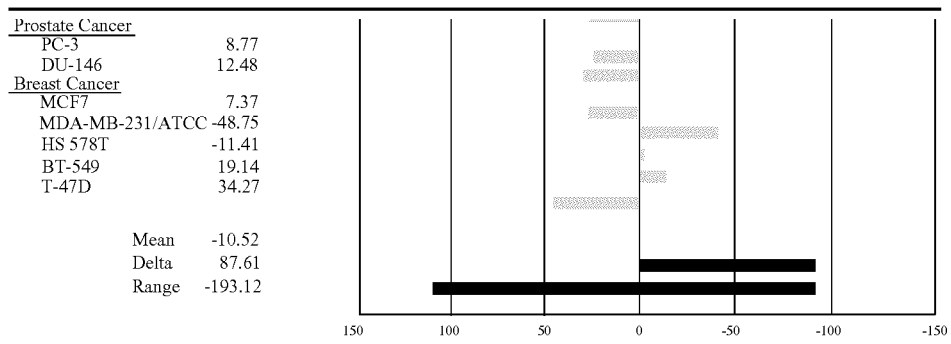

What is claimed is:
1. A compound of the formula

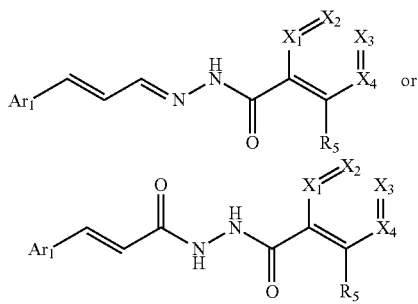

or a pharmaceutically acceptable salt thereof; wherein $Ar_1$ is

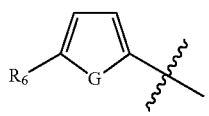

where G is O, N, or S, and $R_6$ is nitro, cyano, —$PO_4$, —CHO, or —COOH; and $Ar_1$ is optionally substituted with one or more substituents independently chosen from cyano, $C_1$-$C_2$alkyl, $C_1$-$C_2$alkoxy, mono- and di-($C_1$-$C_2$)alkylamino, $C_1$-$C_2$haloalkyl, and $C_1$-$C_2$haloalkoxy;

$X_1$ is $CR_1$ or N;
$X_2$ is $CR_2$ or N;
$X_3$ is $CR_3$ or N;
$X_4$ is $CR_4$ or N;
wherein

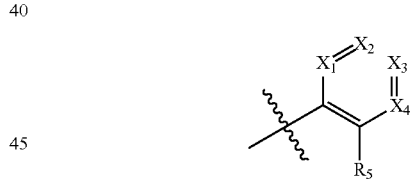

is not unsubstituted or substituted phenyl, unsubstituted pyridyl, or unsubstituted pyridazine, or 2-methylbenzo[d]thiazole, and no more than 2 of $X_1$-$X_4$ are N;

$R_1$ to $R_4$ are independently chosen from hydrogen, halogen, hydroxyl, cyano, nitro, $C_1$-$C_4$alkyl, $C_1$-$C_4$alkoxy, mono- and di-($C_1$-$C_4$)alkylamino, $C_1$-$C_2$haloalkyl, and $C_1$-$C_2$haloalkoxy; and One of the following three conditions may be present:

$R_1$ and $R_2$ may be taken together to form a 6-membered carbocyclic ring, or a 5- or 6-membered heterocyclic ring containing 1 or 2 heteroatoms independently chosen from N, O, and S, which carbocyclic or heterocyclic $R_1$/$R_2$ ring is substituted with 0 or 1 or more substituents independently chosen from halogen, hydroxyl, amino, cyano, nitro, $C_1$-$C_4$alkyl, $C_1$-$C_4$alkoxy, mono- and di-($C_1$-$C_4$)alkylamino, $C_1$-$C_2$haloalkyl, and $C_1$-$C_2$haloalkoxy;

$R_2$ and $R_3$ may be taken together to form a 6-membered carbocyclic ring, or a 5- or 6-membered heterocyclic ring containing 1 or 2 heteroatoms independently chosen from N, O, and S, which carbocyclic or heterocyclic $R_2/R_3$ ring is substituted with 0 or 1 or more substituents independently chosen from halogen, hydroxyl, amino, cyano, nitro, $C_1$-$C_4$alkyl, $C_1$-$C_4$alkoxy, mono- and di-($C_1$-$C_4$)alkylamino, $C_1$-$C_2$haloalkyl, and $C_1$-$C_2$haloalkoxy;

$R_3$ and $R_4$ may be taken together to form a 6-membered carbocyclic ring, or a 5- or 6-membered heterocyclic ring containing 1 or 2 heteroatoms independently chosen from N, O, and S, which carbocyclic or heterocyclic $R_3/R_4$ ring is substituted with 0 or 1 or more substituents independently chosen from halogen, hydroxyl, amino, cyano, nitro, $C_1$-$C_4$alkyl, $C_1$-$C_4$alkoxy, mono- and di-($C_1$-$C_4$)alkylamino, $C_1$-$C_2$haloalkyl, and $C_1$-$C_2$haloalkoxy; and $R_5$ is hydrogen, halogen, hydroxyl, amino, cyano, nitro, $C_1$-$C_4$alkyl, $C_1$-$C_4$alkoxy, mono- or di-($C_1$-$C_4$)alkylamino, $C_1$-$C_2$haloalkyl, or $C_1$-$C_2$haloalkoxy.

2. A compound or salt of claim 1, where $Ar_1$ is

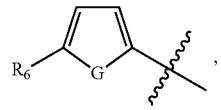

where $R_6$ is nitro and G is oxygen.

3. A compound or salt of claim 1, wherein
$R_1$ to $R_4$ are independently chosen from hydrogen, halogen, hydroxyl, nitro, $C_1$-$C_2$alkyl, $C_1$-$C_2$alkoxy, mono- or di-($C_1$-$C_2$)alkylamino, trifluoromethyl, and trifluoromethoxy; and
one of the following two conditions is present:
$R_2$ and $R_3$ are taken together to form a 6-membered aromatic ring or 6-membered heteroaromatic ring containing one or two nitrogen atoms, which 6-membered $R_2/R_3$ ring is substituted with 0 or 1 or more substituents independently chosen from halogen, hydroxyl, nitro, $C_1$-$C_2$alkyl, $C_1$-$C_2$alkoxy, mono- and di-($C_1$-$C_2$)alkylamino, trifluoromethyl, and trifluoromethoxy;
$R_3$ and $R_4$ are taken together to form a 6-membered aromatic ring or 6-membered heteroaromatic ring containing one or two nitrogen atoms, which 6-membered $R_3/R_4$ ring is substituted with 0 or 1 or more substituents independently chosen from halogen, hydroxyl, nitro, $C_1$-$C_2$alkyl, $C_1$-$C_2$alkoxy, mono- and di-($C_1$-$C_2$)alkylamino, trifluoromethyl, and trifluoromethoxy; and
$R_5$ is hydrogen or hydroxyl.

4. A compound or salt of claim 3, wherein
$X_1$ is $CR_1$, $X_4$ is $CR_4$; $R_5$ is hydroxyl; and
$X_2$ is $CR_2$; $X_3$ is $CR_3$ and $R_2$ and $R_3$ are taken together to form a 6-membered aromatic ring, which 6-membered $R_2/R_3$ ring is substituted with 0 or 1 or more substituents independently chosen from halogen, hydroxyl, nitro, $C_1$-$C_2$alkyl, $C_1$-$C_2$alkoxy, mono- and di-($C_1$-$C_2$)alkylamino, trifluoromethyl, and trifluoromethoxy.

5. A compound or salt of claim 3, wherein
$X_1$ is N; $X_2$ is $CR_2$; $R_5$ is hydroxyl; and
$X_3$ is $CR_3$; $X_4$ is $CR_4$; and $X_3$ and $X_4$ are taken together to form a 6-membered aromatic ring, which 6-membered $R_3/R_4$ ring is substituted with 0 or 1 or more substituents independently chosen from halogen, hydroxyl, nitro, $C_1$-$C_2$alkyl, $C_1$-$C_2$alkoxy, mono- and di-($C_1$-$C_2$)alkylamino, trifluoromethyl, and trifluoromethoxy.

6. A compound or salt of claim 3, wherein
$X_1$ is $CR_1$; $X_2$ is N; $R_5$ hydroxyl; and
$X_3$ is $CR_3$; $X_4$ is $CR_4$; and $X_3$ and $X_4$ are taken together to form a 6-membered aromatic ring, which 6-membered $R_3/R_4$ ring is substituted with 0 or 1 or more substituents independently chosen from halogen, hydroxyl, nitro, $C_1$-$C_2$alkyl, $C_1$-$C_2$alkoxy, mono- and di-($C_1$-$C_2$)alkylamino, trifluoromethyl, and trifluoromethoxy.

7. A compound of claim 1 or salt thereof, wherein the compound has the formula

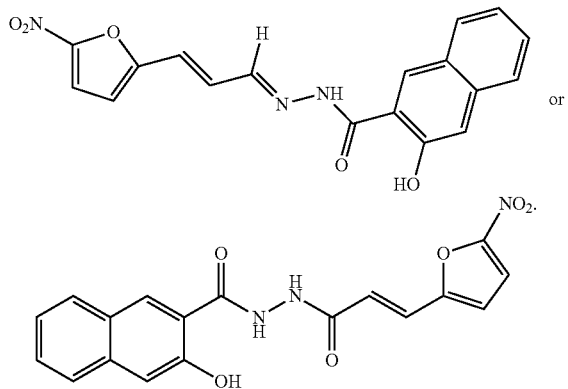

8. A method of treating mantle cell lymphoma, leukemia, non-small cell lung cancer, colon cancer, CNS cancer, melanoma, ovarian cancer, renal cancer, prostate cancer, or breast cancer in a subject comprising providing to the subject a therapeutically effective amount of a compound or pharmaceutically acceptable salt thereof of the formula

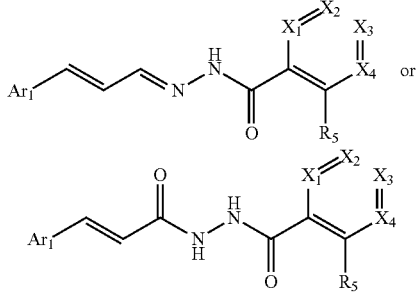

where
$Ar_1$ is

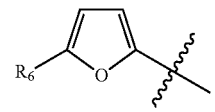

where G is O, N, or S, and $R_6$ is nitro, cyano, —$PO_4$, —CHO, or —COOH; and
$Ar_1$ is optionally substituted with one or more substituents independently chosen from cyano, $C_1$-$C_2$alkyl, $C_1$-$C_2$alkoxy, mono- and di-($C_1$-$C_2$)alkylamino, $C_1$-$C_2$haloalkyl, and $C_1$-$C_2$haloalkoxy;
$X_1$ is $CR_1$ or N;
$X_2$ is $CR_2$ or N;
$X_3$ is $CR_3$ or N;
$X_4$ is $CR_4$ or N;

wherein

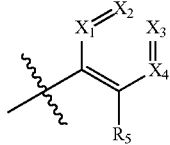

is not unsubstituted or substituted phenyl, unsubstituted pyridyl, or unsubstituted pyridazine, or 2-methylbenzo[d]thiazole, and no more than 2 of $X_1$-$X_4$ are N;

$R_1$ to $R_4$ are independently chosen from hydrogen, halogen, hydroxyl, amino, cyano, nitro, $C_1$-$C_4$alkyl, $C_1$-$C_4$alkoxy, mono- and di-$(C_1$-$C_4)$alkylamino, $C_1$-$C_2$haloalkyl, and $C_1$-$C_2$haloalkoxy;

One of the following three conditions may be present:

$R_1$ and $R_2$ may be taken together to form a 6-membered carbocyclic ring, or a 5- or 6-membered heterocyclic ring containing 1 or 2 heteroatoms independently chosen from N, O, and S, which carbocyclic or heterocyclic $R_1$/$R_2$ ring is substituted with 0 or 1 or more substituents independently chosen from halogen, hydroxyl, amino, cyano, nitro, $C_1$-$C_4$alkyl, $C_1$-$C_4$alkoxy, mono- and di-$(C_1$-$C_4)$alkylamino, $C_1$-$C_2$haloalkyl, and $C_1$-$C_2$haloalkoxy;

$R_2$ and $R_3$ may be taken together to form a 6-membered carbocyclic ring, or a 5- or 6-membered heterocyclic ring containing 1 or 2 heteroatoms independently chosen from N, O, and S, which carbocyclic or heterocyclic $R_2$/$R_3$ ring is substituted with 0 or 1 or more substituents independently chosen from halogen, hydroxyl, amino, cyano, nitro, $C_1$-$C_4$alkyl, $C_1$-$C_4$alkoxy, mono- and di-$(C_1$-$C_4)$alkylamino, $C_1$-$C_2$haloalkyl, and $C_1$-$C_2$haloalkoxy;

$R_3$ and $R_4$ may be taken together to form a 6-membered carbocyclic ring, or a 5- or 6-membered heterocyclic ring containing 1 or 2 heteroatoms independently chosen from N, O, and S, which carbocyclic or heterocyclic $R_3$/$R_4$ ring is substituted with 0 or 1 or more substituents independently chosen from halogen, hydroxyl, amino, cyano, nitro, $C_1$-$C_4$alkyl, $C_1$-$C_4$alkoxy, mono- and di-$(C_1$-$C_4)$alkylamino, $C_1$-$C_2$haloalkyl, and $C_1$-$C_2$haloalkoxy; and $R_5$ is hydrogen, halogen, hydroxyl, amino, cyano, nitro, $C_1$-$C_4$alkyl, $C_1$-$C_4$alkoxy, mono- or di-$(C_1$-$C_4)$alkylamino, $C_1$-$C_2$haloalkyl, or $C_1$-$C_2$haloalkoxy.

9. The method of claim 8, wherein the compound is a compound of the formula

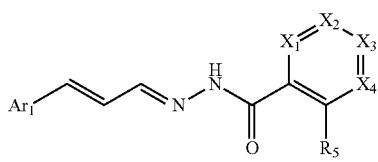

or a pharmaceutically acceptable salt thereof.

10. The method of claim 9 wherein $Ar_1$ is a 2-furanyl which is substituted with at least one nitro, —CHO, —COOH, or —PO$_4$ substituent and optionally substituted with one or more substituents independently chosen from cyano, $C_1$-$C_2$alkyl, $C_1$-$C_2$alkoxy, mono- and di-$(C_1$-$C_2)$alkylamino, $C_1$-$C_2$haloalkyl, and $C_1$-$C_2$haloalkoxy.

11. The method of claim 9, wherein the compound is a compound of the formula

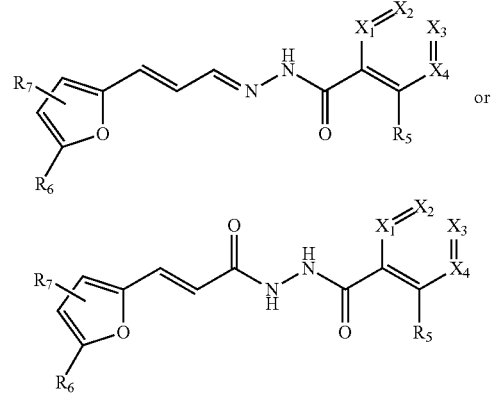

or a pharmaceutically acceptable salt thereof, wherein $R_6$ is nitro, cyano, —CHO, —COOH, or —PO$_4$; and $R_7$ is 0, 1, or 2 substituents independently chosen from halogen, $C_1$-$C_2$alkyl, and $C_1$-$C_2$alkoxy.

12. The method of claim 11, wherein $R_6$ is nitro and $R_7$ is absent.

13. The method of claim 8, wherein

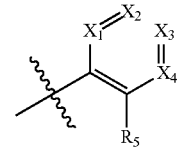

is a phenyl, naphthyl, quinolinyl, isoquinolinyl, or pyridyl, in which $R_5$ is hydrogen, halogen, hydroxyl, amino, cyano, nitro, $C_1$-$C_4$alkyl, $C_1$-$C_4$alkoxy, mono- or di-$(C_1$-$C_4)$alkylamino, $C_1$-$C_2$haloalkyl, or $C_1$-$C_2$haloalkoxy; and each of which phenyl, naphthyl, quinolinyl, isoquinolinyl, is substituted with 0, 1, or 2 substituents independently chosen from halogen, hydroxyl, amino, cyano, nitro, $C_1$-$C_4$alkyl, $C_1$-$C_4$alkoxy, mono- and di-$(C_1$-$C_4)$alkylamino, $C_1$-$C_2$haloalkyl, and $C_1$-$C_2$haloalkoxy.

14. The method of claim 13, wherein $R_5$ is hydrogen or hydroxyl; and each of which phenyl, naphthyl, quinolinyl, isoquinolinyl, is substituted with 0, 1, or 2 substituents independently chosen from chloro, bromo, hydroxyl, nitro, methyl, methoxy, and trifluoromethyl.

15. The method of claim 13, wherein

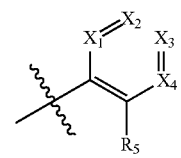

is phenyl, 3-pyridyl, 2-, 3-, or 4-hydroxy phenyl, 3-hydroxy-naphth-2-yl, 1-hydroxy-isoquinolin-3-yl, 4-hydroxy-quinolin-3-yl;

each of which is additionally substituted with 0, 1, or 2 substituents independently chosen from hydroxyl, nitro, chloro, bromo, methyl, methoxy, and trifluoromethyl.

16. The method of claim 13, wherein

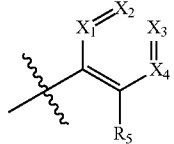

is 3-hydroxy-naphth-2-yl.

17. The method of claim 8, wherein $Ar_1$ is nitro-phenyl or nitro-furanyl.

18. The method of claim 8, wherein $Ar_1$ is

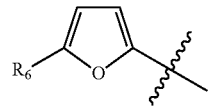

and $R_6$ is nitro, cyano, —$PO_4$, —CHO, or —COOH.

19. The method of claim 18, wherein $R_6$ is nitro.

20. The method of claim 8, wherein the disease or disorder is leukemia, non-small cell lung cancer, colon cancer, ovarian cancer, renal cancer, prostate cancer, or breast cancer.

* * * * *

SEQUENCE LISTING

<160> NUMBER OF SEQ ID NOS: 1

<210> SEQ ID NO 1
<211> LENGTH: 62
<212> TYPE: DNA
<213> ORGANISM: Artificial Sequence
<220> FEATURE:
<223> OTHER INFORMATION: Hj NOXA Luciferase

<400> SEQUENCE: 1
gatcccggtg cacgtttcat caatttgttc aagagacaaa ttgatgaaac gtgcaccttt     60
tt                                                                    62